(12) United States Patent
Nakagawa et al.

(10) Patent No.: US 12,361,541 B2
(45) Date of Patent: Jul. 15, 2025

(54) MEASUREMENT APPARATUS AND MEASUREMENT METHOD

(71) Applicant: HITACHI HIGH-TECH CORPORATION, Tokyo (JP)

(72) Inventors: Hiromitsu Nakagawa, Tokyo (JP); Takeshi Tanaka, Tokyo (JP); Daisuke Fukui, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 604 days.

(21) Appl. No.: 17/642,903

(22) PCT Filed: Aug. 27, 2020

(86) PCT No.: PCT/JP2020/032451
§ 371 (c)(1),
(2) Date: Mar. 14, 2022

(87) PCT Pub. No.: WO2021/131159
PCT Pub. Date: Jul. 1, 2021

(65) Prior Publication Data
US 2022/0366560 A1 Nov. 17, 2022

(30) Foreign Application Priority Data

Dec. 26, 2019 (JP) .................. 2019-236325

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/0077* (2013.01); *A61B 5/1114* (2013.01);
(Continued)

(58) Field of Classification Search
None
See application file for complete search history.

(56) References Cited

U.S. PATENT DOCUMENTS 10,832,045 B2 * 11/2020 Murray ................ G06V 40/103
2006/0120564 A1 6/2006 Imagawa et al.
(Continued)

FOREIGN PATENT DOCUMENTS

CN 1842824 A 10/2006
CN 109919137 A 6/2019
(Continued)

OTHER PUBLICATIONS

Kamel et al., "Efficient Body Motion Quantification and Similarity Evaluation Using 3-D Joints Skeleton Coordinates", IEEE Transactions on Systems, Man, and Cybernetics: Systems, May 31, 2019, pp. 2774-2788, vol. 51, No. 5 (15 pages).
(Continued)

*Primary Examiner* — Leon Flores
(74) *Attorney, Agent, or Firm* — Foley & Lardner LLP

(57) ABSTRACT

Provided is a measurement apparatus including a processor and a storage unit. The storage unit holds measurement data of each time point which is obtained by a photographing apparatus, and temporal-spatial constraints. The processor extracts a position of an object from the measurement data of each time point, determines whether the object satisfies the temporal-spatial constraints, and determines, based on a result of the determination on whether the object satisfies the temporal-spatial constraints, whether the object is an analysis target.

8 Claims, 16 Drawing Sheets

(51) Int. Cl.
  *A61B 5/11*   (2006.01)
  *G06T 7/50*   (2017.01)
  *G06T 7/73*   (2017.01)
(52) U.S. Cl.
  CPC .......... *A61B 5/1128* (2013.01); *A61B 5/7203* (2013.01); *G06T 7/50* (2017.01); *G06T 7/73* (2017.01); *G06T 2207/10016* (2013.01); *G06T 2207/10028* (2013.01); *G06T 2207/30008* (2013.01)

(56) References Cited

U.S. PATENT DOCUMENTS

| | | |
|---|---|---|
| 2016/0282215 A1 | 9/2016 | Naito et al. |
| 2019/0236374 A1 | 8/2019 | Nakagawa et al. |
| 2021/0192224 A1* | 6/2021 | Nakagawa ............. G06V 20/40 |

FOREIGN PATENT DOCUMENTS

| | | |
|---|---|---|
| JP | 2005-276010 A | 10/2005 |
| JP | 2016-179171 A | 10/2016 |
| JP | 2017-202236 A | 11/2017 |
| JP | 2019-121904 A | 7/2019 |
| KR | 20150004461 A | 1/2015 |
| WO | WO-2017/130902 A1 | 8/2017 |

OTHER PUBLICATIONS

Extended European Search Report issued in corresponding European Patent Application No. 20905149.9, dated Nov. 7, 2023 (12 pages).

Rueangsirarak et al., "Automatic Musculoskeletal and Neurological Disorder Diagnosis With Relative Joint Displacement From Human Gait", IEEE Transactions on Neural Systems and Rehabilitation Engineering, Dec. 1, 2018, pp. 2387-2396, vol. 26, No. 12 (10 pages).

International Search Report with English translation and Written Opinion issued in corresponding application No. PCT/JP2020/032451 dated Oct. 20, 2020.

Office Action issued in corresponding Chinese Patent Application No. 202080056914.3, dated Apr. 14, 2023 (8 pages).

* cited by examiner

MEASUREMENT DB
230
DEPTH TABLE 231

| MEASUREMENT TIME | PIXEL 1 | PIXEL 2 | PIXEL 3 | ... |
|---|---|---|---|---|
| 2019/06/30 15:00:00.00 | 3398 | 3380 | 3382 | ... |
| 2019/06/30 15:00:00.03 | 3398 | 3380 | 3383 | ... |
| 2019/06/30 15:00:00.06 | 3398 | 3380 | 3384 | ... |
| 2019/06/30 15:00:00.09 | 3398 | 3381 | 3388 | ... |
| 2019/06/30 15:00:00.12 | 3398 | 3380 | 3387 | ... |
| 2019/06/30 15:00:00.15 | 3397 | 3380 | 3384 | ... |
| 2019/06/30 15:00:00.18 | 3398 | 3380 | 3382 | ... |
| 2019/06/30 15:00:00.21 | 3397 | 3381 | 3383 | ... |
| 2019/06/30 15:00:00.24 | 3398 | 3380 | 3382 | ... |
| 2019/06/30 15:00:00.27 | 3399 | 3380 | 3382 | ... |
| 2019/06/30 15:00:00.30 | 3400 | 3380 | 3382 | ... |
| ... | ... | ... | ... | ... |

SKELETON COORDINATE TABLE 232

| MEASUREMENT TIME | PERSON | JOINT 1 | JOINT 2 | ... |
|---|---|---|---|---|
| 2019/06/30 15:00:10.00 | P1 | (0.11,-0.01,2.74) | (0.10,0.20,2.45) | ... |
| 2019/06/30 15:00:10.00 | P2 | (-0.12,0.04,2.55) | (-0.09,0.32,2.46) | ... |
| 2019/06/30 15:00:10.03 | P1 | (0.10,-0.01,2.74) | (0.11,-0.01,2.74) | ... |
| 2019/06/30 15:00:10.03 | P2 | (-0.12,0.04,2.55) | (-0.09,0.32,2.46) | ... |
| 2019/06/30 15:00:10.06 | P1 | (0.11,-0.01,2.74) | (0.11,-0.01,2.74) | ... |
| 2019/06/30 15:00:10.06 | P2 | (-0.11,0.04,2.55) | (-0.09,0.32,2.46) | ... |
| ... | ... | ... | ... | ... |

*FIG.3*

DETERMINATION DB
240

TEMPORAL CONSTRAINT TABLE

241

| START TIME (241-1) | END TIME (241-2) | TIME RATIO (241-3) |
|---|---|---|
| 5 SECONDS | 15 SECONDS | 80% |

SPATIAL CONSTRAINT TABLE

242

| LONGITUDINAL RANGE (242-1) | LATERAL RANGE (242-2) | SPACE RATIO (242-3) |
|---|---|---|
| (2,5) | (-1,1) | 90% |

DETERMINATION RESULT TABLE

243

| PERSON (243-1) | TEMPORAL MATCHING RATIO (243-2) | SPATIAL MATCHING RATIO (243-3) |
|---|---|---|
| P1 | 62% | 92% |
| P2 | 93% | 99% |
| P3 | 90% | 12% |

FIG.4

ANALYSIS DB
250

ANALYSIS TARGET TABLE

| MEASUREMENT TIME | PERSON | JOINT 1 | JOINT | ... |
|---|---|---|---|---|
| 2019/06/30 15:00:10.00 | P2 | (-0.12,0.04,2.55) | (-0.09,0.32,2.46) | ... |
| 2019/06/30 15:00:10.03 | P2 | (-0.12,0.04,2.55) | (-0.09,0.32,2.46) | ... |
| 2019/06/30 15:00:10.06 | P2 | (-0.11,0.04,2.55) | (-0.09,0.32,2.46) | ... |
| 2019/06/30 15:00:10.09 | P2 | (-0.12,0.04,2.55) | (-0.09,0.32,2.45) | ... |
| 2019/06/30 15:00:10.12 | P2 | (-0.12,0.04,2.55) | (-0.09,0.32,2.46) | ... |
| 2019/06/30 15:00:10.15 | P2 | (-0.13,0.04,2.55) | (-0.09,0.31,2.46) | ... |
| ... | ... | ... | ... | ... |

DETERMINATION DB
1130

PITCH TABLE 1131

| PERSON (1131-1) | PITCH (1131-2) | START TIME (1131-3) | END TIME (1131-4) |
|---|---|---|---|
| P1 | 1 | 2019/06/30 15:00:10.00 | 2019/06/30 15:00:11.23 |
| P1 | 2 | 2019/06/30 15:00:11.23 | 2019/06/30 15:00:12.49 |
| P2 | 1 | 2019/06/30 15:00:10.00 | 2019/06/30 15:00:10.00 |
| P2 | 2 | 2019/06/30 15:00:10.00 | 2019/06/30 15:00:10.60 |
| P2 | 3 | 2019/06/30 15:00:10.60 | 2019/06/30 15:00:11.20 |
| ... | ... | ... | ... |

TEMPORAL-SPATIAL CONSTRAINT TABLE 1132

| TYPE (1132-1) | SELECTED (1132-2) | PITCH (1132-3) | LONGITUDINAL RANGE (1132-4) | LATERAL RANGE (1132-5) | TEMPORAL-SPATIAL MATCHING RATIO (1132-6) |
|---|---|---|---|---|---|
| NATURAL WALK | TRUE | 50% | (2,5) | (-2,0) | 90% |
| NATURAL WALK | TRUE | 100% | (2,5) | (0,2) | 80% |
| KNEE-BENT | FALSE | 50% | (2,5) | (-2,0) | 70% |
| KNEE-BENT | FALSE | 100% | (2,5) | (0,2) | 70% |

DETERMINATION RESULT TABLE 1133

| PERSON (1133-1) | PITCH (1133-2) | TEMPORAL-SPATIAL MATCHING RATIO (1133-3) |
|---|---|---|
| P1 | 50% | 100% |
| P1 | 100% | 0% |
| P2 | 50% | 96% |
| P2 | 100% | 90% |
| P3 | 50% | 0% |
| P3 | 100% | 3% |

*FIG.12*

MEASUREMENT APPARATUS AND MEASUREMENT METHOD

CLAIM OF PRIORITY

The present application claims priority from Japanese patent application JP2019-236325 filed on Dec. 26, 2019, the content of which is hereby incorporated by reference into this application.

BACKGROUND OF THE INVENTION

This invention relates to measurement of data.

In recent years, people looking ahead to the future of a super-aging society are increasingly more conscious of health, and a healthcare industry is thus drawing attention. This is accompanied by a steady advance in utilization of information technology (IT) in medical practice, with new business fields and medical services including regenerative medicine equipment, nursing-care robots, and insurance guidance service assistance being developed one after another.

Preventive medicine services, in particular, are one of fields on which great expectations are placed with a look ahead to geriatric medicine. Prevention medicine is a concept of clarifying health risks that may fall on anyone in old age and continuously practicing activities that maintain or promote health to prevent a person from becoming sick, as opposed to a concept of treating a person after he or she becomes sick.

In order to clarify health risks and check effects of health maintaining/promoting activities, quantification of health condition by measurement is required. Users can now each measure for the quantification in his or her everyday life owing to advancement in Internet of Things (IoT) technology and wearable devices.

Meanwhile, a large amount of measurement data obtained in everyday life often includes noise, and consequently has a problem in that selection of an analysis target is difficult. For instance, in a case of analysis of a video photographed in a public place, the noise gives difficulty to uniform determination of which data is to be an analysis target.

In JP 2017-202236 A, there is disclosed measurement of a lumbar area, which moves little in walk, for the purpose of obtaining data that has less noise. This can reduce occurrence of measurement noise.

In JP 2016-179171 A, there is disclosed removal of a case in which a following point jumps and other cases of rapid change as noise. This can reduce occurrence of measurement noise.

SUMMARY OF THE INVENTION

The technology of JP 2017-202236 A can reduce noise due to a measurement error, but has a problem in that analysis sites are limited.

The technology of JP 2016-179171 A is effective for removal of noise due to a measurement error, but is not much effective for noise due to video capturing an unintended object.

An object of this invention is therefore to extract required measurement data without affecting a method of analysis even in an environment prone to noise due to a measurement error and noise due to video capturing an unintended object.

To solve at least one of the foregoing problems, one aspect of this invention is a measurement apparatus, comprising a processor; and a storage unit, the storage unit being configured to hold measurement data of each time point which is obtained by a photographing apparatus, and temporal-spatial constraints, the processor being configured to extract a position of an object from the measurement data of each time point, determine whether the object satisfies the temporal-spatial constraints, and determine, based on a result of the determination on whether the object satisfies the temporal-spatial constraints, whether the object is an analysis target.

According to the at least one aspect of this invention, required measurement data can be extracted without affecting the method of analysis even in the environment prone to the noise due to the measurement error and the noise due to video capturing an unintended object. Objects, configurations, and effects other than those described above are revealed in the following description of embodiments.

BRIEF DESCRIPTION OF THE DRAWINGS

FIG. 3 is an illustration of configurations of tables to be stored in a measurement DB in the first embodiment.

FIG. 4 is an illustration of configurations of tables to be stored in a determination DB in the first embodiment.

FIG. 5 is an illustration of a configuration of a table to be stored in an analysis DB in the first embodiment.

FIG. 12 is an illustration of tables to be stored in a determination DB in the second embodiment.

DETAILED DESCRIPTION OF THE PREFERRED EMBODIMENTS

Figure 1:
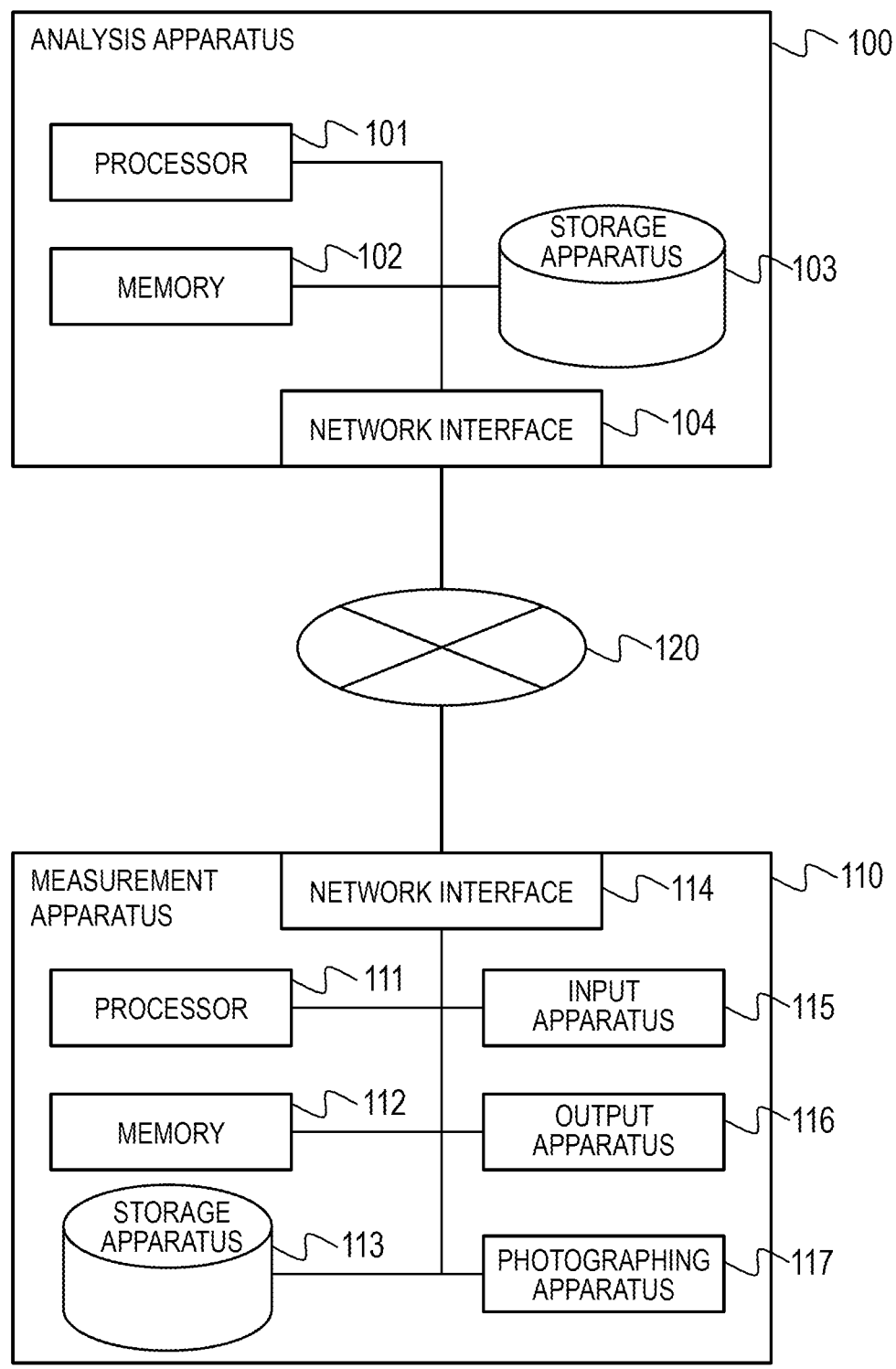
FIG. 1 is an illustration of a physical configuration of an overall system in a first embodiment of this invention.

Embodiments of this invention are described below with reference to the accompanying drawings. However, it should be noted that the embodiments are merely examples for achieving this invention and do not limit a technical scope of this invention.

In the following description, "interface unit" refers to one or more interface apparatus. The one or more interface apparatus may be one or more interface apparatus of the same type (for example, one or more network interface cards (NICs)), or may be interface apparatus of two or more different types (for example, an NIC and a hot bus adapter (HBA)).

In the following description, "storage unit" refers to one or more memories. At least one memory may be a volatile memory or a non-volatile memory. The storage unit may include, in addition to the one or more memories, one or more PDEVs. "PDEV" means a physical storage apparatus, typically, a non-volatile storage apparatus (for example, an auxiliary storage apparatus). The one or more PDEVs are, for example, hard disk drives (HDDs) or solid state drives (SSDs).

In the following description, "processor unit" refers to one or more processors. At least one processor is typically a central processing unit (CPU). The one or more processors may include a hardware circuit executing some or all of processing.

In the following description, an expression "kkk unit/module" (excluding the interface unit, the storage unit, and the processor unit) is used in some places to describe a function. However, a function may be implemented by execution of one or more computer programs by the processor unit, or may be implemented by one or more hardware circuits (for example, field-programmable gate arrays (FPGAs) or application-specific integrated circuits (ASICs)). When a function is implemented by execution of one or more programs by the processor unit, predetermined processing is executed with appropriate use of the storage unit and/or the interface unit, or others, and the function may therefore be considered at least a part of the processor unit. Processing described with a function as a subject of a predicate may be processing executed by the processor unit or by an apparatus including the processor unit. The one or more programs may be installed from a program source. The program source may be, for example, a program distribution computer or a computer-readable recording medium (for example, a non-transitory recording medium). Descriptions of functions are an example, and a plurality of functions may be integrated into one function or one function may be divided into a plurality of functions.

In the following description, "xxx table" or a similar expression is used in some places to describe information. However, information may have any data structure. In other words, "xxx table" can be rephrased as "xxx information" in order to indicate that the information is independent of data structure. In the following description, configurations of tables are an example, and one table may be divided into two or more tables, and all or some of two or more tables may be one table.

In the following description, "time" is expressed in the form of year, month, day, hour, minute, second. However, a rougher or finer unit of time may be used, or a different unit of time may be used.

In the following description, "data set" means data (a logical chunk of electronic data) including one or more data elements, for example, any one of a record, a file, a key-value pair, and a tuple.

First Embodiment

FIG. 1 is an illustration of a physical configuration of an overall system in a first embodiment of this invention.

The system in the first embodiment includes an analysis apparatus 100 and a measurement apparatus 110 coupled to each other via a network 120.

The analysis apparatus 100 is an apparatus for analyzing data. The analysis apparatus 100 includes a network interface 104, a memory 102, and a storage apparatus 103, as well as a processor 101 coupled to those.

The processor 101 executes various types of processing by controlling, as required, the units and modules included in the analysis apparatus 100 in accordance with a program stored in the memory 102.

The memory 102 is a semiconductor memory, for example, a dynamic random access memory (DRAM), and stores, among others, a program executed by the processor 101, data referred to in processing executed by the processor 101 in accordance with the program, and data generated as a result of the processing executed by the processor 101.

The storage apparatus 103 is, for example, an HDD or an SSD, and stores various types of data to be used in the processing executed by the processor 101. For example, the program and the data described above may be stored in the storage apparatus 103 so that at least a part of those is copied to the memory 102, or the data may be updated on the memory 102 to be copied to the storage apparatus 103 as required.

The network interface 104 is coupled to the network 120 and holds communication to and from the measurement apparatus 110 over the network 120.

The measurement apparatus 110 is an apparatus for measuring data. The measurement apparatus 110 includes a network interface 114, a memory 112, a storage apparatus 113, an input apparatus 115, an output apparatus 116, and a photographing apparatus 117, as well as a processor 111 coupled to those.

The processor 111 executes various types of processing by controlling, as required, the units and modules included in the measurement apparatus 110 in accordance with a program stored in the memory 112.

The memory 112 is a semiconductor memory, for example, a DRAM, and stores, among others, a program executed by the processor 111, data referred to in processing executed by the processor 111 in accordance with the program, and data generated as a result of the processing executed by the processor 111.

The storage apparatus 113 is, for example, an HDD or an SSD, and stores various types of data to be used in the processing executed by the processor 111. For example, the program and the data described above may be stored in the storage apparatus 113 so that at least a part of those is copied to the memory 112, or the data may be updated on the memory 112 to be copied to the storage apparatus 113 as required.

The network interface 114 is coupled to the network 120 and holds communication to and from the analysis apparatus 100 over the network 120.

The input apparatus 115 is an apparatus for receiving input of information from a user of the measurement apparatus 110, and may include, for example, at least one of a keyboard, a mouse, or a touch panel.

The output apparatus 116 is an apparatus for outputting information to the user of the measurement apparatus 110, and may include, for example, at least one of an image display apparatus or a printer.

The photographing apparatus 117 may be any apparatus which photographs a measurement target and obtains a video of the measurement target. For example, the photographing apparatus 117 may be a regular RGB camera, an infrared camera, or the like which photographs a two-dimensional video, and may also be a depth camera capable of obtaining depth information for each pixel in addition to a two-dimensional video.

Figure 2:
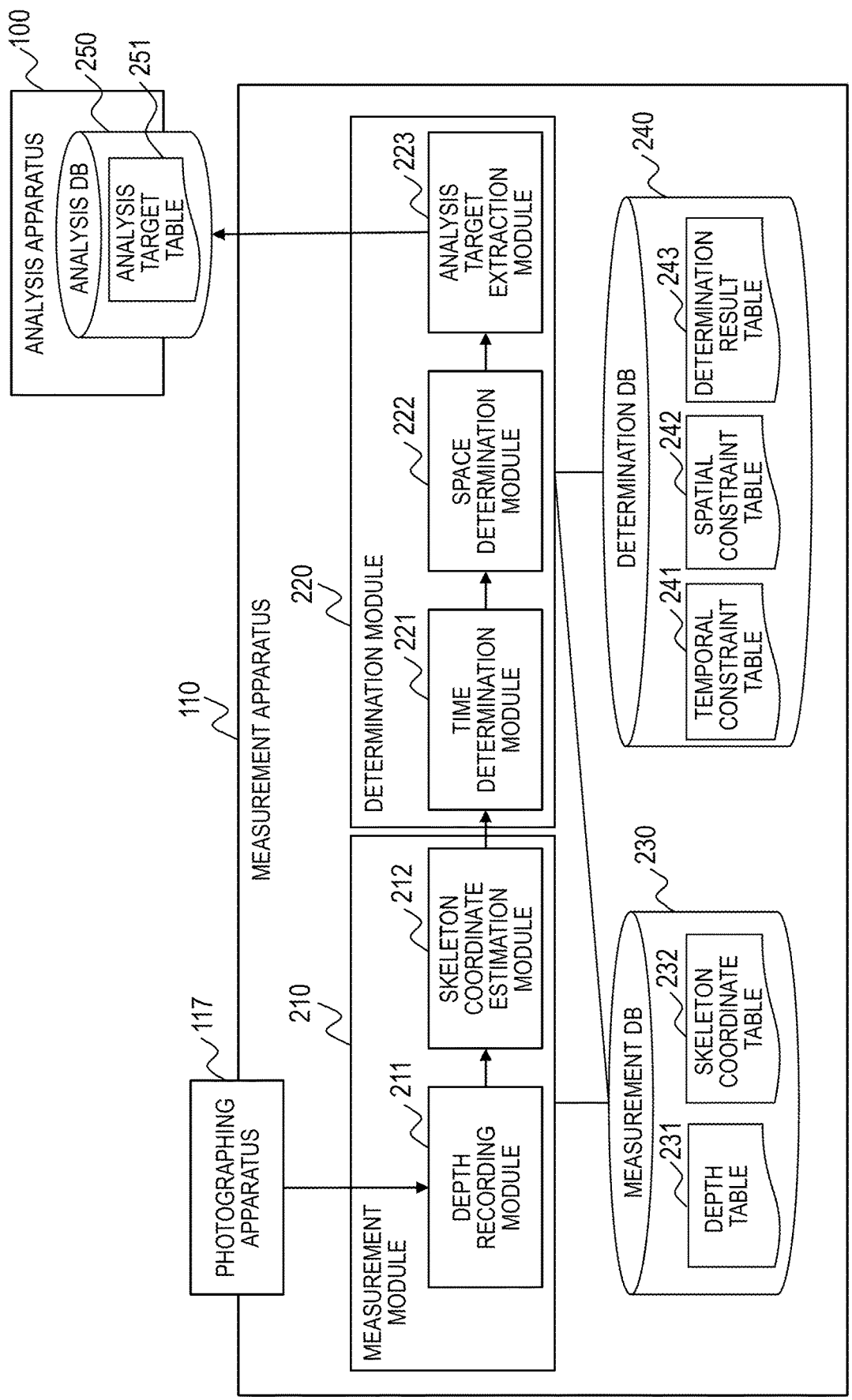
FIG. 2 is an illustration of a logical configuration of the overall system in the first embodiment.

FIG. 2 is an illustration of a logical configuration of the overall system in the first embodiment.

The measurement apparatus 110 includes a measurement module 210, a determination module 220, a measurement database (DB) 230, and a determination DB 240. The measurement module 210 includes a depth recording module 211 and a skeleton coordinate estimation module 212. The determination module 220 includes a time determination module 221, a space determination module 222, and an analysis target extraction module 223. The measurement module 210 and the determination module 220 are each a function block implemented by the processor 111 of the measurement apparatus 110 by execution of a program stored in the memory 112. In other words, processing executed by the measurement module 210 or the determination module 220 in the following description is actually executed by the processor 111 in accordance with a program stored in the memory 112.

The measurement DB 230 and the determination DB 240 are stored in the storage apparatus 113 of the measurement apparatus 110. The measurement DB 230 includes a depth table 231 and a skeleton coordinate table 232. Details of those are described later with reference to FIG. 3. The determination DB 240 includes a temporal constraint table 241, a spatial constraint table 242, and a determination result table 243. Details of those are described later with reference to FIG. 4.

The analysis apparatus 100 includes an analysis DB 250. The analysis DB 250 is stored in the storage apparatus 103 of the analysis apparatus 100. The analysis DB 250 includes an analysis target table 251. Details of the analysis target table 251 are described later with reference to FIG. 5.

The depth recording module 211 of the measurement module 210 extracts depth information from video data of a video photographed by the photographing apparatus 117, and records the depth information in the depth table 231. An example in which the photographing apparatus 117 is a depth camera is given here. Details of processing of the depth recording module 211 are described later with reference to FIG. 6.

The skeleton coordinate estimation module 212 of the measurement module 210 refers to the depth table 231 to estimate skeleton coordinates for each photographed person, and records results of the estimation in the skeleton coordinate table 232. Details of processing of the skeleton coordinate estimation module 212 are described later with reference to FIG. 7.

The time determination module 221 of the determination module 220 refers to the skeleton coordinate table 232 and the temporal constraint table 241 to calculate a temporal matching ratio for each photographed person, and records results of the calculation in the determination result table 243. Details of processing of the time determination module 221 are described later with reference to FIG. 8.

The space determination module 222 of the determination module 220 refers to the skeleton coordinate table 232 and the spatial constraint table 242 to calculate a spatial matching ratio for each photographed person, and records results of the calculation in the determination result table 243. Details of processing of the space determination module 222 are described later with reference to FIG. 9.

The analysis target extraction module 223 of the determination module 220 refers to the skeleton coordinate table 232 and the determination result table 243 to extract skeleton coordinate data about a person who is an analysis target, and transmits the extracted data to the analysis apparatus 100. The analysis apparatus 100 records the data received from the analysis target extraction module 223 in the analysis target table 251. Details of processing of the analysis target extraction module 223 are described later with reference to FIG. 10.

An example of measurement and analysis that use the measurement apparatus 110 and the analysis apparatus 100 of the first embodiment is now described. For example, there is assumed a case in which a person who is an analysis target is asked to perform predetermined movement (walk or the like) and is photographed during the movement with the photographing apparatus 117 (a depth camera or the like), and measurement data obtained from the photographing is used to analyze motor function and the like of the person. In this situation, it is not always the case that only the person who is an analysis target is present in a photographing range of the photographing apparatus 117. For instance, there is a case in which staff performing photographing, a person assisting the analysis target person, a passerby who has nothing to do with the photographing, or the like is photographed along with the analysis target person.

The measurement module 210 extracts, from the measurement data, skeleton coordinates of each person at each time. The determination module 220 determines, for each person, from skeleton coordinates at each time, whether the person is an analysis target, and outputs skeleton coordinates of a person determined to be an analysis target to the analysis apparatus 100. The analysis apparatus 100 may execute any form of analysis processing, and description of analysis processing executed by the analysis apparatus 100 is omitted in the first embodiment.

FIG. 3 is an illustration of configurations of tables to be stored in the measurement DB 230 in the first embodiment.

As illustrated in FIG. 2, the measurement DB 230 stores the depth table 231 and the skeleton coordinate table 232. The depth table 231 includes, for example, as shown in FIG. 3, a plurality of records each corresponding to one frame of a video. Each record includes a measurement time 231-1 and depth information for each pixel (for example, a depth 231-2 of Pixel 1, a depth 231-3 of Pixel 2, a depth 231-4 of Pixel 3, and so on).

The measurement time 231-1 is a time at which the frame of the record has been photographed. The depth information including the depth 231-2 to the depth 231-4 indicates a depth for each pixel in the frame of the record, that is, a distance from the photographing apparatus 117 to a photographing target corresponding to the pixel. Although omitted in FIG. 3, depth information of all pixels in the frame of the record is actually recorded in the depth table 231.

The skeleton coordinate table 232 includes, for example, as shown in FIG. 3, a plurality of records, and each record includes information of skeleton coordinates of one person included in one frame of a video. Specifically, each record includes a measurement time 232-1, a person 232-2, and information of skeleton coordinates for each person (for example, coordinates 232-3 of the person's Joint 1, coordinates 232-4 of the person's Joint 2, and so on).

The measurement time 232-1 is a time at which the frame of the record has been photographed. The person 232-2 is identification information of the person included in the frame of the record. The coordinates 232-3 of Joint 1, the coordinates 232-4 of Joint 4, and so on are each coordinate values of a position of that joint of the person included in the frame of the record (for example, three-dimensional coordinate values indicating the position of a photographing target in a space). Although omitted in FIG. 3, coordinate values of all joints extracted from the person included in the frame of the record are actually recorded in the skeleton coordinate table 232.

In the example of FIG. 3, two persons are extracted from one frame photographed at 15:00:10 on Jun. 30, 2019, identification information "P1" and identification information "P2" are assigned to the two persons, respectively, and coordinate values of each joint in each of the two persons are recorded.

FIG. 4 is an illustration of configurations of tables to be stored in the determination DB 240 in the first embodiment.

As illustrated in FIG. 2, the determination DB 240 stores the temporal constraint table 241, the spatial constraint table 242, and the determination result table 243.

In the temporal constraint table 241, information indicating temporal constraints for selecting an analysis target is recorded. Specifically, the temporal constraint table 241 includes, for example, as shown in FIG. 4, a start time 241-1, an end time 241-2, and a time ratio 241-3.

The start time 241-1 and the end time 241-2 are information specifying a start point and an end point of a time slot that serves as a reference for determining whether a person included in a video is an analysis target, and the time ratio 241-3 is information indicating a threshold value for a proportion of records included in the time slot (namely, the temporal matching ratio). Details of determination in which those pieces of information are referred to are described later with reference to FIG. 8.

In the spatial constraint table 242, information indicating spatial constraints for selecting an analysis target is recorded. Specifically, the spatial constraint table 242 includes, for example, as shown in FIG. 4, a longitudinal range 242-1, a lateral range 242-2, and a space ratio 242-3.

The longitudinal range 242-1 and the lateral range 242-2 are information specifying a space range that serves as a reference for determining whether a person included in a video is an analysis target, and the space ratio 242-3 is information indicating a threshold value for a proportion of records included in the space range (namely, the spatial matching ratio). Details of determination in which those pieces of information are referred to are described later with reference to FIG. 9.

In the determination result table 243, results of calculation which is executed by referring to the skeleton coordinate table 232, the temporal constraint table 241, and the spatial constraint table 242 in order to determine whether a person included in a video is an analysis target are recorded. Specifically, the determination result table 243 includes, for example, as shown in FIG. 4, a person 243-1, a temporal matching ratio 243-2, and a spatial matching ratio 243-3.

The person 243-1 is identification information of each person included in a video, and corresponds to the person 232-2 of the skeleton coordinate table 232. A temporal matching ratio and a spatial matching ratio calculated for each person are recorded as the temporal matching ratio 243-2 and the spatial matching ratio 243-3, respectively. Details of those calculations are described later with reference to FIG. 10.

An example of setting the temporal constraint table 241 and the spatial constraint table 242 is now described. Here, an example in which predetermined movement to be performed by a person who is an analysis target is "walk" is described. Specifically, in the described example, an analysis target person is asked to start walking along a predetermined walking course in response to a cue from a photographer, and is photographed during the walk with the photographing apparatus 117, and the photographing is stopped when the walk along the walking course is finished.

In this case, when it is assumed that a length of time from the start of the photographing to a point at which the analysis target person actually starts walking in response to a cue is approximately 5 seconds, and that the walk along the walking course is finished at 15 seconds since the start of the photographing, "5 seconds" and "15 seconds" are set to the start time 241-1 and the end time 241-2, respectively.

In this case, the analysis target person starts walking in response to the cue and the photographing stops when the walk is finished, and it is accordingly assumed that most of data about the analysis target person out of data obtained by the photographing is contained within a time range between the 5-second point and the 15-second point described above. On the other hand, data about a non-analysis target person that is included in the data obtained by the photographing is assumed to be low in ratio at which the data is contained within this time range (namely, the temporal matching ratio), because that person is assumed to be moving about independently of the cue, or be captured in the photographing range for the moment. The time ratio 241-3 is a threshold value for determining a person who is an analysis target based on the temporal matching ratio, and a value appropriate for the determination (in the example of FIG. 4, "80%") is set thereto.

Coordinate values indicating a range of the walking course described above are set to the longitudinal range 242-1 and the lateral range 242-2. For example, when a position in a space photographed by the photographing apparatus 117 is specified by coordinate values of a Cartesian coordinate system, a coordinate value on one axis may be set as the longitudinal range 242-1, and a coordinate value on an axis orthogonal to the one axis may be set as the lateral range 242-2. However, this method of specifying the range of the space is an example, and other methods may be used to specify the range of the space.

In this case also, the analysis target person intends to walk along the walking course, and it is accordingly assumed that most positions in the data about the analysis target person out of the data obtained by the photographing are contained within the range of the space described above. On the other hand, positions indicated by data about a non-analysis target person that is included in the data obtained by the photographing are assumed to be low in ratio at which the positions are contained within this range of the space (namely, the spatial matching ratio), because that person is assumed to be walking a little off the walking course when that person is, for example, a staff member or a person assisting the analysis target person, or assumed to walk along the walking course only momentarily when that person is a passerby. The space ratio 242-3 is a threshold value for determining a person who is an analysis target based on the spatial matching ratio, and a value appropriate for the determination (in the example of FIG. 4, "90%") is set thereto.

The information recorded in the temporal constraint table 241 and the information recorded in the spatial constraint table 242 are an example of temporal-spatial constraints. Although the temporal-spatial constraints in the first embodiment are temporal constraints and spatial constraints that are set independently of each other, temporal constraints and spatial constraints may be set in association with each other. An example of the latter is described later in a second embodiment of this invention.

FIG. 5 is an illustration of a configuration of a table to be stored in the analysis DB 250 in the first embodiment.

As illustrated in FIG. 2, the analysis DB 250 stores the analysis target table 251. In the analysis target table 251, a record about a person determined to be an analysis target is recorded out of records stored in the skeleton coordinate table 232. Specifically, each record of the analysis target table 251 includes a measurement time 251-1, a person 251-2, coordinates 251-3 of Joint 1, coordinates 251-4 of Joint 2, and others. Those correspond to the measurement time 232-1, the person 232-2, the coordinates 232-3 of Joint 1, the coordinates 232-4 of Joint 2, and others of the skeleton coordinate table 232, respectively. However, unlike the skeleton coordinate table 232, the analysis target table 251 includes only records about a person determined to be an analysis target (in the example of FIG. 5, a person "P2").

Figure 6:
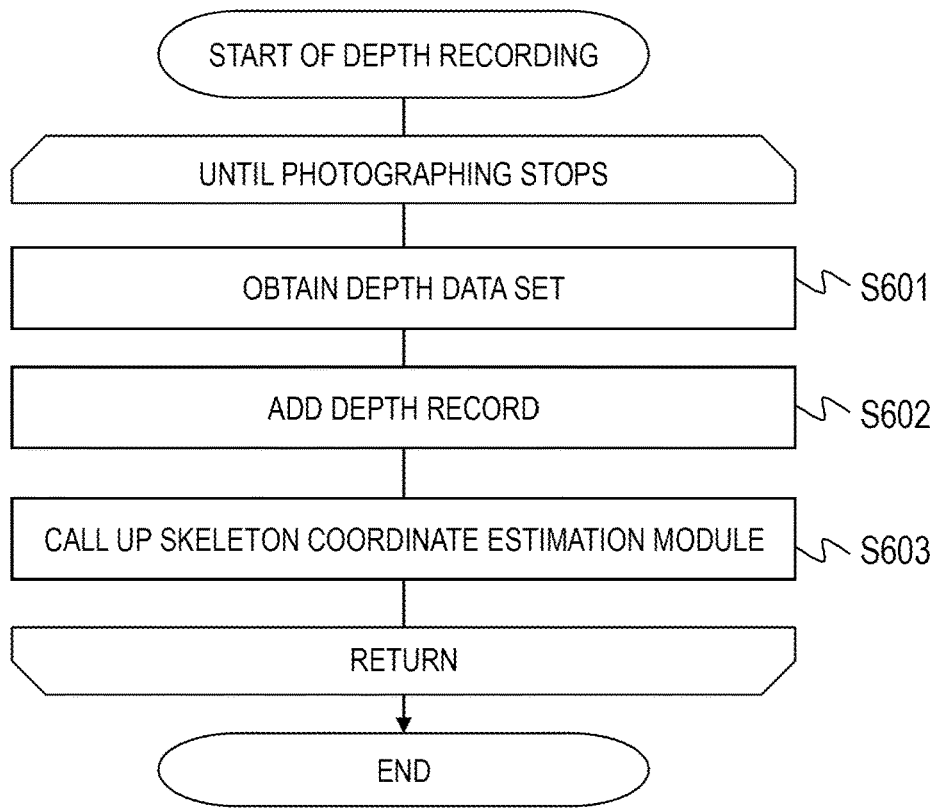
FIG. 6 is a flow chart for illustrating the processing of a depth recording module in the first embodiment.

FIG. 6 is a flow chart for illustrating the processing of the depth recording module 211 in the first embodiment.

The depth recording module 211 starts depth recording by obtaining data of a video photographed by the photographing apparatus 117 and, once the depth recording is started, repeatedly executes Step S601 to Step S603 below until the photographing stops.

The depth recording module 211 first obtains a depth data set from the photographing apparatus 117 (Step S601). The depth recording module 211 next adds a record to the depth table 231 to record the obtained depth data set (Step S602). A record including a measurement time of the obtained depth data set and depth information of each pixel that is associated with the measurement time is thus added to the depth table 231. The depth recording module 211 next calls up the skeleton coordinate estimation module 212 (Step S603). The processing of the depth recording module 211 ends when the photographing stops.

Figure 7:
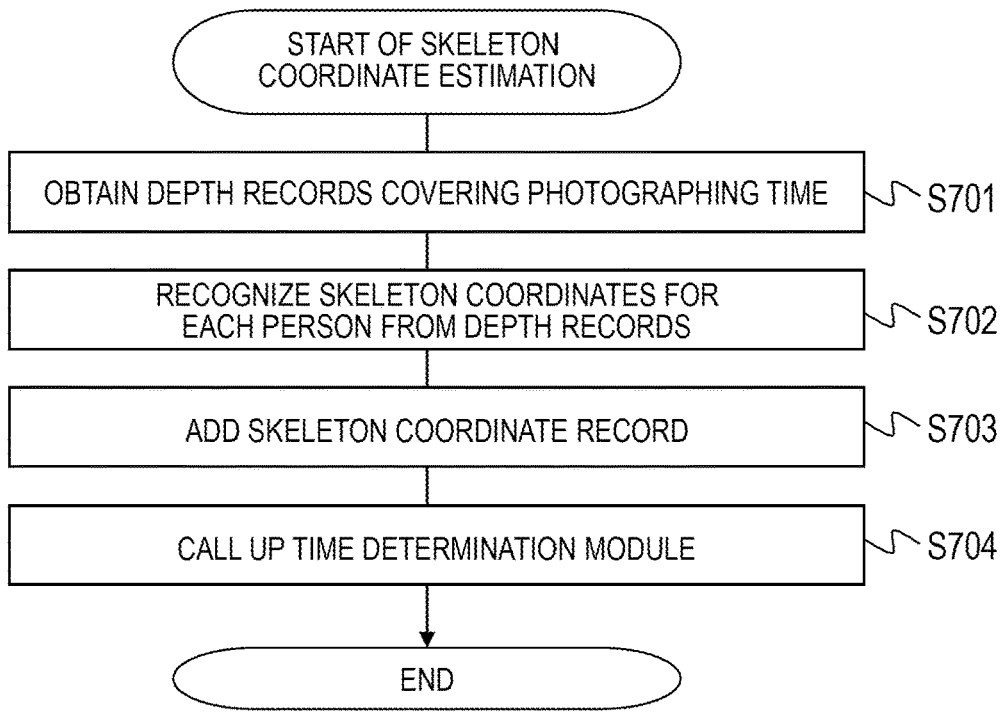
FIG. 7 is a flow chart for illustrating the processing of a skeleton coordinate estimation module in the first embodiment.

FIG. 7 is a flow chart for illustrating the processing of the skeleton coordinate estimation module 212 in the first embodiment.

The skeleton coordinate estimation module 212 first obtains, from the depth table 231, records covering a photographing time (Step S701). The skeleton coordinate estimation module 212 next recognizes skeleton coordinates for each person from the obtained records (Step S702). In this step, the skeleton coordinate estimation module 212 can use a known depth recognition model, and description of a detailed method of recognition is therefore omitted.

The skeleton coordinate estimation module 212 next adds a record including coordinate values obtained as a result of the skeleton coordinate recognition to the skeleton coordinate table 232 (Step S703). The skeleton coordinate estimation module 212 next calls up the time determination module 221 (Step S704), and ends the processing.

FIG. 6 and FIG. 7 described above are an example of processing executed when the photographing apparatus 117 is a depth camera. However, as described above, the photographing apparatus 117 may be a regular RGB camera or the like that does not measure depth. In that case, the measurement module 210 records video information obtained from the photographing apparatus 117 in the measurement DB 230. For example, RGB values are recorded for each pixel instead of the depth of each pixel in a frame in the depth table 231. The skeleton coordinate estimation module 212 estimates skeleton coordinates by referring to RGB values of each frame and using an image recognition model. In this estimation, the skeleton coordinate estimation module 212 can use, for example, OpenPose or any other known recognition model.

Figure 8:
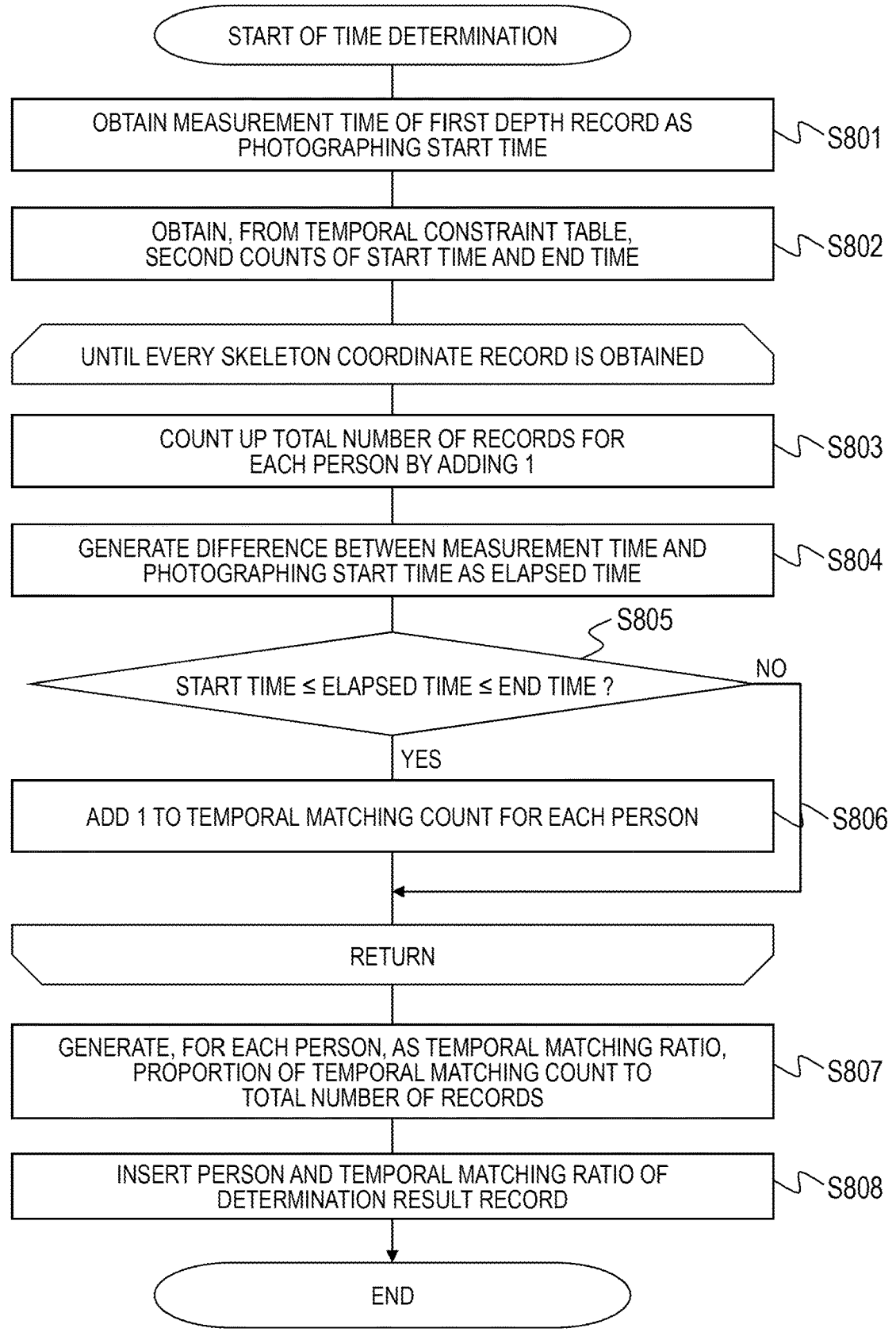
FIG. 8 is a flow chart for illustrating the processing of a time determination module in the first embodiment.

FIG. 8 is a flow chart for illustrating the processing of the time determination module 221 in the first embodiment.

The time determination module 221 first obtains the measurement time 321-1 of the first record in the depth table 231 as a photographing start time (Step S801). For example, when the depth table 231 is as shown in FIG. 3, 15:00:00:00, Jun. 30, 2019, which is the value of the measurement time 321-1 of the first record, is obtained.

The time determination module 221 next obtains second counts of the start time 241-1 and the end time 241-2 from the temporal constraint table 421 (Step S802). For example, when the temporal constraint table 421 is as shown in FIG. 4, 5 seconds and 15 seconds are obtained as the second count of the start time 241-1 and the second count of the end time 241-2, respectively.

The time determination module 221 next executes the processing steps of Step S803 to Step S806 below until every record in the skeleton coordinate table 232 is obtained. First, the time determination module 221 obtains a record that has not been obtained from the skeleton coordinate table 232, refers to the person 232-2 of this record, and counts up the total number of records associated with that person by adding 1 (Step S803).

The time determination module 221 next calculates a difference between the measurement time 232-1 of this record and the photographing start time obtained in Step S801 to generate an elapsed time since the start of the photographing (Step S804). In the example of FIG. 3 and FIG. 4 described above, the elapsed time of each record with 15:00:00:00, Jun. 30, 2019 as Time 0 is generated in this manner.

The time determination module 221 next determines, about this record, whether the elapsed time calculated in Step S804 is within a range from the start time obtained in Step S802 to the end time obtained in Step S802 (in the example described above, equal to or more than 5 seconds and equal to or less than 15 seconds) (Step S805).

When it is determined in Step S805 that the elapsed time is within the range from the start time to the end time (Step S805: "Yes"), the time determination module 221 adds 1 to a temporal matching count of the person associated with this record (Step S806). When it is determined in Step S805 that the elapsed time is outside the range from the start time to the end time (Step S805: "No"), on the other hand, the time determination module 221 does not execute Step S806 for this record.

When the processing steps of Step S803 to Step S806 described above are finished for every record in the skeleton coordinate table 232, it means that the total number of records in the skeleton coordinate table 232 has been counted for each person, and that the number of records having the elapsed time within the range from the start time to the end time has also been counted for each person as the temporal matching count.

The time determination module 221 next calculates, for each person, a proportion of the temporal matching count to the total number of records as the temporal matching ratio (Step S807).

The time determination module 221 next records, for each person, the temporal matching ratio of the person in a record of the determination result table 243 that is associated with the person as the temporal matching ratio 243-2 (Step S808).

This concludes the processing of the time determination module 221.

Figure 9:
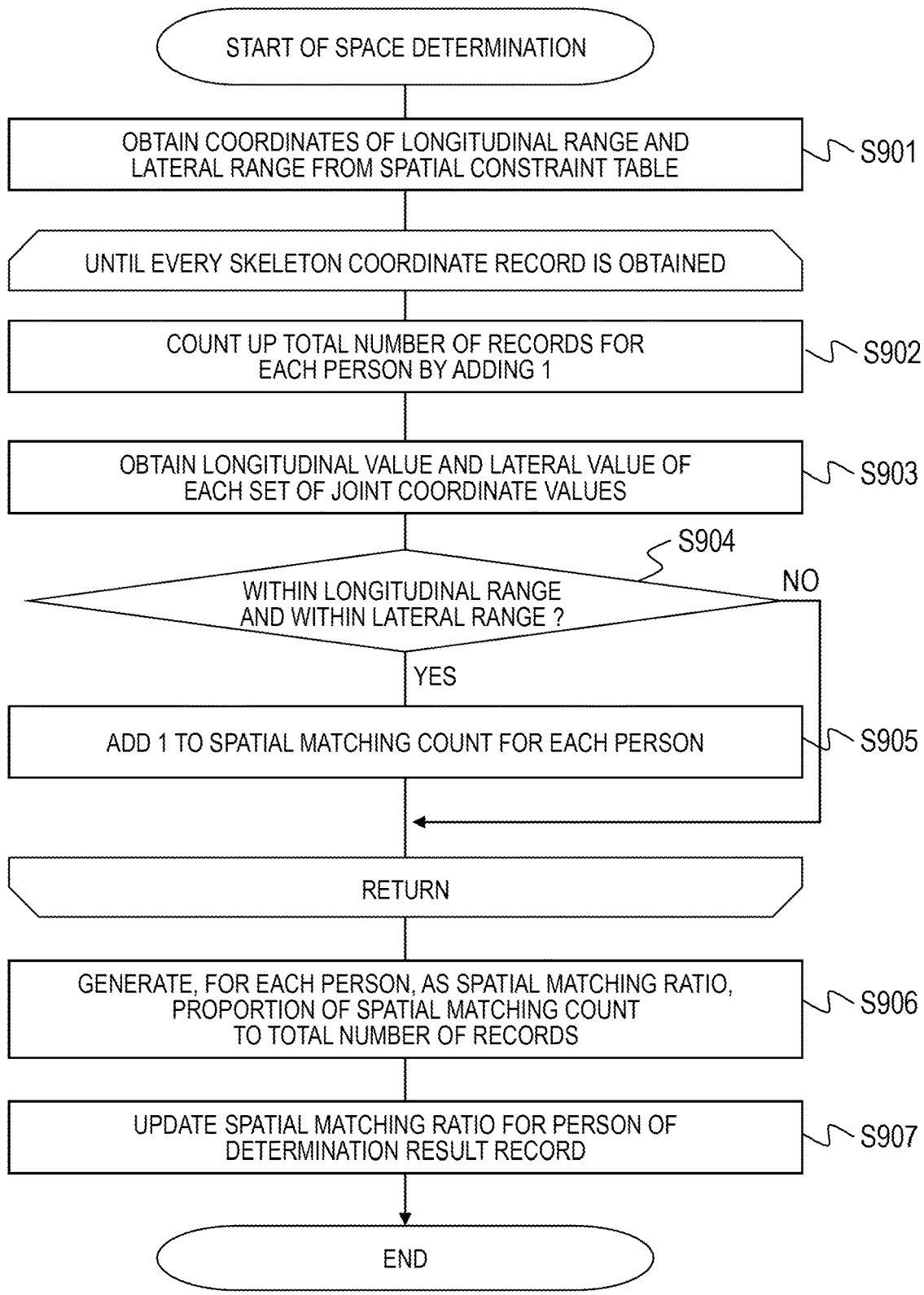
FIG. 9 is a flow chart for illustrating the processing of a space determination module in the first embodiment.

FIG. 9 is a flow chart for illustrating the processing of the space determination module 222 in the first embodiment.

The space determination module 222 first obtains coordinates of the longitudinal range 242-1 and the lateral range 242-2 from the spatial constraint table 242 (Step S901). For example, when the spatial constraint table 242 is as shown in FIGS. 4, (2, 5) and (−1, 1) are obtained as coordinates of the longitudinal range 242-1 and coordinates of the lateral range 242-2, respectively.

The space determination module 222 next executes the processing steps of Step S902 to Step S905 below until every record in the skeleton coordinate table 232 is obtained. First, the space determination module 222 obtains a record that has not been obtained from the skeleton coordinate table 232, refers to the person 232-2 of this record, and counts up the total number of records associated with that person by adding 1 (Step S902).

The space determination module 222 next obtains a longitudinal value and a lateral value of each set of joint coordinate values of this record (Step S903). Specifically, the space determination module 222 obtains, out of each set of joint coordinate values, a value on the same coordinate axis as a coordinate axis of the longitudinal range 242-1 of the spatial constraint table 242, and a value on the same coordinate axis as a coordinate axis of the lateral range 242-2.

The space determination module 222 next compares each set of joint coordinate values obtained in Step S903 and the longitudinal range and the lateral range obtained in Step S901 to determine whether the longitudinal value of the set of joint coordinate values is contained within the longitudinal range, and whether the lateral value of the set of joint coordinate values is contained within the lateral range (Step S904).

One record of the skeleton coordinate table 232 includes a plurality of sets of joint coordinate values of one person. In Step S904, the space determination module 222 may determine whether all of the plurality of sets of joint coordinate values are contained within the longitudinal range and the lateral range, may determine whether a predetermined proportion of or a predetermined number of sets of coordinate values are contained within the longitudinal range and the lateral range, or may determine whether coordinate values of joints in one or more predetermined sites are contained within the longitudinal range and the lateral range.

The comparison between the longitudinal value of the coordinates and the longitudinal range 242-1 of the spatial constraint table 242 and between the lateral value of the coordinates and the lateral range 242-2 described above is an example of the method of determining whether an obtained position of a person is contained within a predetermined space range, and methods other than the method described above may be used for the determination.

When it is determined in Step S904 that the joint coordinate values are contained within the longitudinal range and the lateral range (Step S904: "Yes"), the space determination module 222 adds 1 to a spatial matching count of the person associated with this record (Step S905). When it is determined in Step S904 that the joint coordinate values are not contained within the longitudinal range and the lateral range (Step S904: "No"), the space determination module 222 does not execute Step S905 for this record.

When the processing steps of Step S902 to Step S905 described above are finished for every record in the skeleton coordinate table 232, it means that the total number of records in the skeleton coordinate table 232 has been counted for each person, and that the number of records having joint coordinate values contained within the longitudinal range and the lateral range has also been counted for each person as the spatial matching count.

The space determination module 222 next calculates, for each person, a proportion of the spatial matching count to the total number of records as the spatial matching ratio (Step S906).

The space determination module 222 next records, for each person, the spatial matching ratio of the person in a record of the determination result table 243 that is associated with the person as the spatial matching ratio 243-3 (Step S907).

This concludes the processing of the space determination module 222.

Figure 10:
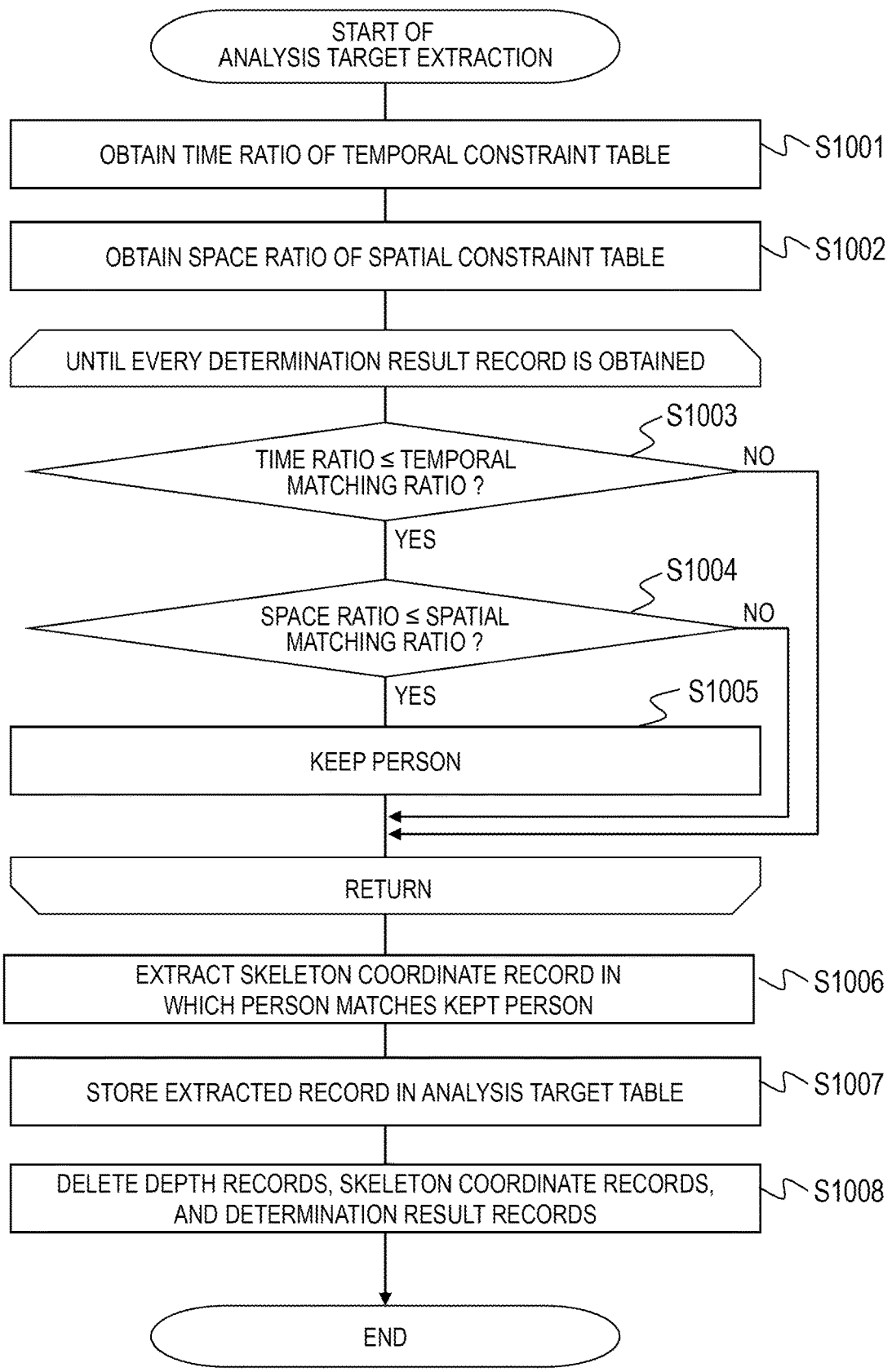
FIG. 10 is a flow chart for illustrating the processing of an analysis target extraction module in the first embodiment.

FIG. 10 is a flow chart for illustrating the processing of the analysis target extraction module 223 in the first embodiment.

The analysis target extraction module 223 first obtains the time ratio 241-3 of the temporal constraint table 241 (Step S1001). The analysis target extraction module 223 next obtains the space ratio 242-3 of the spatial constraint table 242 (Step S1002).

The analysis target extraction module 223 next executes the processing steps of Step S1003 to Step S1005 below until every record in the determination result table 243 is obtained. First, the analysis target extraction module 223 obtains a record that has not been obtained from the determination result table 243 to determine whether the temporal matching ratio 243-2 of this record is equal to or higher than the time ratio 241-3 (Step S1003).

When it is determined in Step S1003 that the temporal matching ratio 243-2 of this record is equal to or higher than the time ratio 241-3 (Step S1003: "Yes"), the analysis target extraction module 223 determines whether the spatial matching ratio 243-3 of this record is equal to or higher than the space ratio 242-3 (Step S1004).

When it is determined in Step S1004 that the spatial matching ratio 243-3 of this record is equal to or higher than the space ratio 242-3 (Step S1004: "Yes"), the analysis target extraction module 223 keeps a person associated with this record (that is, a person identified by the value of the person 243-1 of this record) (Step S1005).

When it is determined in Step S1003 that the temporal matching ratio 243-2 of this record is not equal to or higher than the time ratio 241-3 (Step S1003: "No"), on the other hand, the analysis target extraction module 223 does not execute Step S1004 and Step S1005 for this record. When it is determined in Step S1004 that the spatial matching ratio 243-3 of this record is not equal to or higher than the space ratio 242-3 (Step S1004: "No"), the analysis target extraction module 223 does not execute Step S1005 for this record.

When Step S1003 to Step S1005 described above are finished for every record of the determination result table 243, the analysis target extraction module 223 extracts a record in which identification information of the person kept in Step S1005 is recorded as the person 232-2 from the skeleton coordinate table 232 (Step S1006), and stores the extracted record in the analysis target table 251 (Step S1007). The analysis target table 251 is transmitted to the analysis apparatus 100 and is stored in the analysis DB 250.

The analysis target extraction module 223 then deletes the records finished with the processing described above from the depth table 231, the skeleton coordinate table 232, and the determination result table 243 (Step S1008). This concludes the processing of the analysis target extraction module 223.

In FIG. 10, as illustrated in Step S1003 to Step S1005, a person whose temporal matching ratio is determined to be equal to or higher than the time ratio and whose spatial matching ratio is determined to be equal to or higher than the space ratio is kept as an analysis target. However, this manner of determination is an example, and manners of determination other than the one described above may be executed. For example, determination of the temporal matching ratio and determination of the spatial matching ratio may be assigned different weights, to thereby give importance to a result of any one of the former determination and the latter determination. This accomplishes appropriate extraction of an analysis target by setting a determination condition that is flexibly suited to the situation.

Second Embodiment

The second embodiment of this invention is described next. Except for differences described below, components of a system of the second embodiment have the same functions as the functions of the components of the first embodiment that are denoted by the same reference symbols, and description thereof are therefore omitted.

Figure 11:
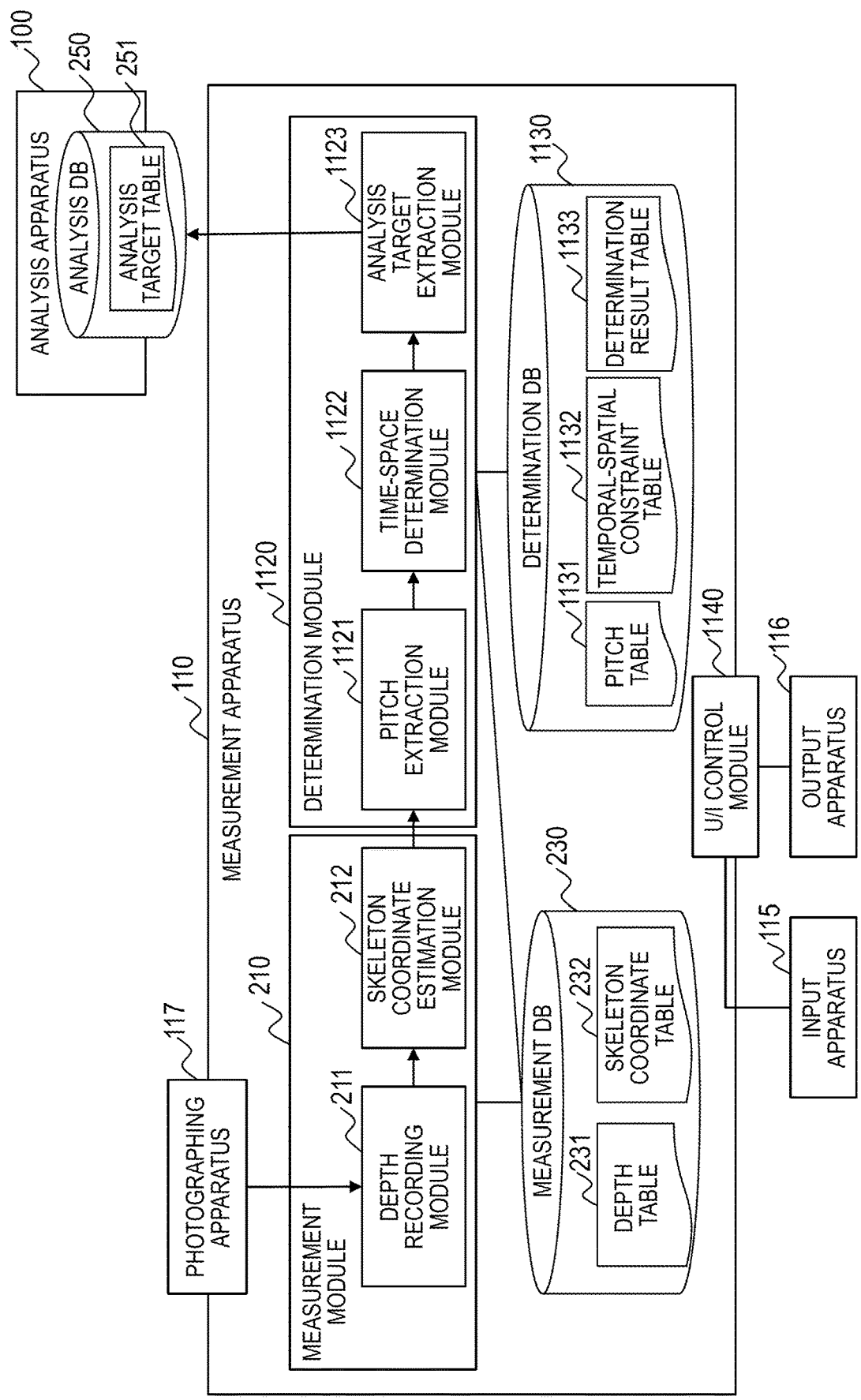
FIG. 11 is an illustration of a logical configuration of an overall system in a second embodiment.

FIG. 11 is an illustration of a logical configuration of an overall system in the second embodiment.

A measurement apparatus 110 of the second embodiment is the same as the measurement apparatus 110 of the first embodiment, except that the determination module 220 and the determination DB 240 are replaced with a determination module 1120 and a determination DB 1130, respectively, and that a user interface (U/I) control module 1140 is included.

The determination DB 1130 is stored in the storage apparatus 113 of the measurement apparatus 110, and includes a pitch table 1131, a temporal-spatial constraint table 1132, and a determination result table 1133. Details of those are described later with reference to FIG. 12.

The determination module 1120 is, as is the determination module 220 in the first embodiment, a function block implemented by the processor 111 of the measurement apparatus 110 by execution of a program stored in the memory 112. The same applies to the U/I control module 1140. In other words, processing executed by the determination module 1120 or the U/I control module 1140 in the following description is actually executed by the processor 111 in accordance with a program stored in the memory 112.

The determination module 1120 includes a pitch extraction module 1121, a time-space determination module 1122, and an analysis target extraction module 1123.

The pitch extraction module 1121 refers to the skeleton coordinate table 232 to extract a cyclic motion, specifies a start time and an end time of the motion, and records the start time and the end time in the pitch table 1131. Details of processing of the pitch extraction module 1121 are described later with reference to FIG. 13.

The time-space determination module 1122 refers to the skeleton coordinate table 232 and the temporal-spatial constraint table 1132 to calculate a temporal-spatial matching ratio for each photographed person, and records results of the calculation in the determination result table 1133. Details of processing of the time-space determination module 1122 are described later with reference to FIG. 14.

The analysis target extraction module 1123 refers to the skeleton coordinate table 232 and the determination result table 1133 to extract skeleton coordinate data about a person who is an analysis target, and transmits the extracted data to the analysis apparatus 100. The analysis apparatus 100 records the data received from the analysis target extraction module 1123 in the analysis target table 251. Details of processing of the analysis target extraction module 1123 are described later with reference to FIG. 15.

The U/I control module 1140 controls display of a user interface screen and reception of information input from a user, which are executed via the input apparatus 115 and the output apparatus 116. Details of processing of the U/I control module 1140 and a user interface to be provided are described later with reference to FIG. 16 and FIG. 17.

FIG. 12 is an illustration of tables to be stored in the determination DB 1130 in the second embodiment.

As illustrated in FIG. 11, the determination DB 1130 stores the pitch table 1131, the temporal-spatial constraint table 1132, and the determination result table 1133.

In the pitch table 1131, for each person whose cyclic motion has been extracted from the skeleton coordinate table 232, information specifying a time of each cycle of the motion is stored. Specifically, the pitch table 1131 includes, as shown in FIG. 12, for example, a person 1131-1, a pitch 1131-2, a start time 1131-3, and an end time 1131-4.

The person 1131-1 is identification information of each person included in a video, and corresponds to the person 232-2 of the skeleton coordinate table 232. The pitch 1131-2 is information indicating an order of a cycle of an extracted cyclic motion. The start time 1131-3 and the end time 11131-4 are pieces of information indicating, for each cycle, a start time and an end time of the cycle, respectively.

For example, records at the top of FIG. 12 and second from the top indicate that a cyclic motion (for example, walk) has been extracted from skeleton coordinates of a person identified by identification information "P1," that a first cycle (namely, a first pitch) of the motion has started at 15:00:10.00 on Jun. 30, 2019, and ended at 15:00:11.23, and that the next cycle (namely, a second pitch) has started at 15:00:11.23 and ended at 15:00:12.49. One pitch corresponds to one cycle that is a unit of repetition, for example, in a case of walk, a cycle starting when a person's left foot touches the ground and ending when the left foot next touches the ground.

In the temporal-spatial constraint table 1132, information indicating temporal and spatial constraints for selecting an analysis target is recorded. Specifically, the temporal-spatial constraint table 1132 includes, as shown in FIG. 12, for example, a type 1132-1, selected 1132-2, a pitch 1132-3, a longitudinal range 1132-4, a lateral range 1132-5, and a temporal-spatial matching ratio 1132-6.

The type 1132-1 indicates a motion type. Examples of motion types include natural walk, knee-bent walk (that is, walk with knees bent and the center of gravity dropped low), and calf raise walk (that is, tiptoe walk).

The selected 1132-2 indicates, for each motion type, whether the motion type has been selected as an extraction target. For example, "True" indicates that the motion type has been selected, and "False" indicates that the motion type has not been selected. In the example of FIG. 12, natural walk is selected and knee-bent walk is not selected.

The pitch 1132-3 is information specifying, when a period in which the extracted cyclic motion has been performed is divided into a plurality of parts, one of the parts.

The longitudinal range 1132-4 and the lateral range 1132-5 are information specifying a range of a space that serves as a reference for determining whether a person included in a video is an analysis target, and are specified for each part of the period in which the extracted cyclic motion has been performed.

The temporal-spatial matching ratio 1132-6 is information indicating a threshold value for a proportion of records contained within a range that is specified by the longitudinal range 1132-4 and the lateral range 1132-5 (namely, the temporal-spatial matching ratio).

For example, according to first two records of the temporal-spatial constraint table 1132 shown in FIG. 12, "natural walk," which is a cyclic motion, is selected as an extraction target. A period in which that motion has been performed (for example, a period starting when an analysis target person starts pre-walk in response to a cue and ending when the person finishes walking) is divided into a part that is 0% to 50% (namely, a first half) and a part that is 50% to 100% (namely, a second half).

As the longitudinal range 1132-4 and the lateral range 1132-5 that are associated with the first half, (2, 5) and (−2, 0) are set, respectively, and "90%" is set as the temporal-spatial matching ratio 1132-6 associated with the first half. As the longitudinal range 1132-4 and the lateral range 1132-5 that are associated with the second half, (2, 5) and (0, 2) are set, respectively, and "80%" is set as the temporal-spatial matching ratio 1132-6 associated with the second half.

The example described above assumes a case in which an analysis target person is asked to start walking from one start point to a turn-around point, turn around at the turn-around point, and walk to a goal point adjacent to the start point, and is photographed during the walk, or a similar case. In other words, the period in which a cyclic motion (for example, natural walk) has been performed corresponds to a period in which the analysis target person walks from the start point to the goal point. The first half of the period corresponds to a part from the start point to the turn-around point, and the second half corresponds to a part from the turn-around point to the goal point.

For example, in the case of setting a cycle that starts when a person's left foot touches the ground and ends when the left foot next touches the ground, or a similar cycle, as one pitch as described above, one pitch corresponds to two steps of walk. When four pitches from Pitch 1 to Pitch 4 are extracted from skeleton coordinates of one person, for example, a period corresponding to the first two pitches (that is, four steps of walk) is identified as the period from the start point to the turn-around point, and a period corresponding to the latter two pitches (that is, four steps of walk) is identified as the period from the turn-around point to the goal point.

For example, in a case in which a walking course for the first half and a walking course for the second half are adjacent to and parallel to each other, or other cases in which different walking courses are set for the first half and the second half, the longitudinal range 1132-4 and the lateral range 1132-5 can be set for each of the walking courses separately. For example, when likelihood of deviating from the walking course differs between the first half and the second half due to presence or absence of a landmark or other factors, the temporal-spatial matching ratio 1132-6 can be set so as to differ between the first half and the second half in order to accommodate the difference in likelihood.

The description given above is an example, and, when a person walks along a straight line from a start point to a goal point once, for example, the pitch-based division described above is not required, and a period from the first pitch to the last pitch can be extracted as the period in which a cyclic motion has been performed. Division into more than two parts may also be executed when, for example, a person walks in a circuit along an outline of a quadrangular area, or walks there and back twice or more in one section.

In the determination result table 1133, results of calculation executed with reference to the skeleton coordinate table 232, the pitch table 1131, and the temporal-spatial constraint table 1132 in order to determine whether a person included in a video is an analysis target are recorded. Specifically, the determination result table 1133 includes, as shown in FIG. 12, for example, a person 1133-1, a pitch 1133-2, and a temporal-spatial matching ratio 1133-3.

The person 1133-1 is identification information of each person included in a video, and corresponds to the person 232-2 of the skeleton coordinate table 232. The pitch 1133-2 is information specifying a part of a period in which an extracted cyclic motion has been performed, and corresponds to the pitch 1132-3 of the temporal-spatial constraint table 1132. For each person, a temporal-spatial matching ratio calculated about the person is recorded as the temporal-spatial matching ratio 1133-3. Details of the calculation are described later with reference to FIG. 14.

Figure 13:
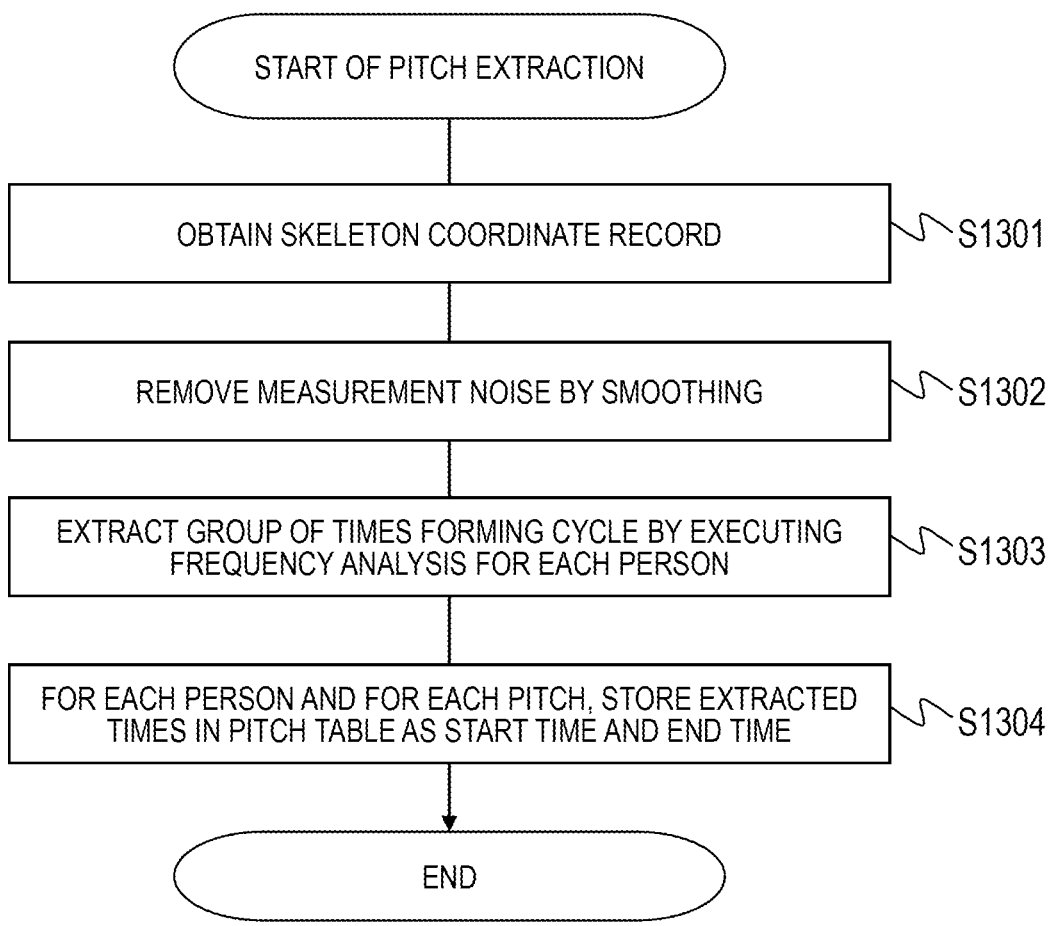
FIG. 13 is a flow chart for illustrating the processing of a pitch extraction module in the second embodiment.

FIG. 13 is a flow chart for illustrating the processing of the pitch extraction module 1121 in the second embodiment.

The pitch extraction module 1121 first obtains a record of the skeleton coordinate table 232 (Step S1301). The pitch extraction module 1121 next removes measurement noise by smoothing (Step S1302). The pitch extraction module 1121 may execute smoothing by, for example, arranging joint coordinates of the obtained record of the skeleton coordinate table 232 in time series for each joint of the person, and calculating a moving average.

The pitch extraction module 1121 next executes, for each person, frequency analysis, to thereby extract a group of times indicating a cycle of the person's motion (Step S1303). The pitch extraction module 1121 may extract a cycle of the person's motion by, for example, performing Fourier transform on data of the smoothed joint coordinates in time series, or other methods.

The pitch extraction module 1121 next stores, for each person and for each pitch, a start time and an end time of the extracted cycle in the pitch table 1131 (Step S1304).

This concludes the processing of the pitch extraction module 1121.

Figure 14:
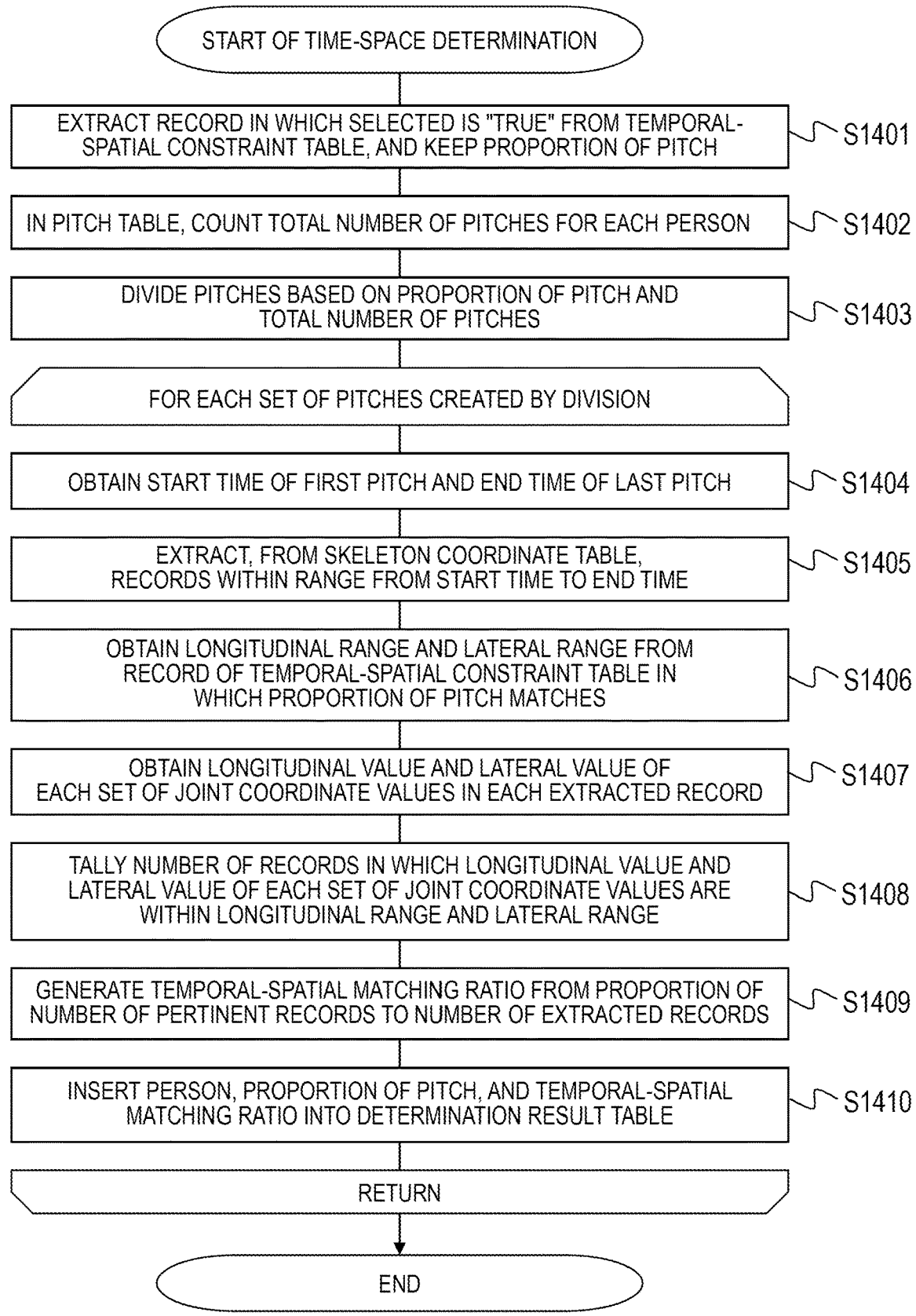
FIG. 14 is a flow chart for illustrating the processing of a time-space determination module in the second embodiment.

FIG. 14 is a flow chart for illustrating the processing of the time-space determination module 1122 in the second embodiment.

The time-space determination module 1122 first refers to the temporal-spatial constraint table 1132 to extract a record in which the selected 1132-2 is "True," and keeps a proportion recorded as the pitch 1132-3 of the extracted record (Step S1401). In the example of FIG. 12, first two records from the top are extracted, and values "50%" and "100%" of the pitch 1132-3 are kept.

The time-space determination module 1122 next refers to the pitch table 1131 to count, for each person, the total number of pitches stored in association with the person (Step S1402). The time-space determination module 1122 next divides the pitches based on the proportion of the pitch that has been kept in Step S1401 and the total number of pitches that has been counted in Step S1402 (Step S1403).

For example, when the pitch table 1131 shown in FIG. 12 is referred to in Step S1402, Pitch 1 and Pitch 2 stored in the first two records are extracted for a person "P1." When it is assumed that, although omitted from FIG. 12, Pitch 3 and Pitch 4 are further stored in the pitch table 1131 in association with the person "P1," four pitches of from Pitch 1 to Pitch 4 are counted in Step S1402. In Step S1403, the four pitches are divided into a set from Pitch 1 to Pitch 2 which corresponds to "0% to 50%" (that is, the first half), and a set from Pitch 3 to Pitch 4 which corresponds to "50% to 100%" (that is, the second half).

The time-space determination module 1122 next executes the processing steps of Step S1404 to Step S1410 below for each set of pitches created by the division.

First, the time-space determination module 1122 selects one of the sets of pitches created by the division, and obtains the start time of the first pitch included in the selected set of pitches and the end time of the last pitch thereof (Step S1404). For example, in the case of the set including Pitch 1 and Pitch 2 of Person P1 of FIG. 12, the value of the start time 1131-3 of Pitch 1 and the value of the end time 1131-4 of Pitch 2 are obtained.

The time-space determination module 1122 next extracts, from the skeleton coordinate table 232, records within a range from the start time to the end time obtained in Step S1404 (Step S1405).

The time-space determination module 1122 next obtains, from the temporal-spatial constraint table 1132, the longitudinal range and the lateral range of a record that holds a selected type and a matching proportion of a pitch (Step S1406). For example, when natural walk is selected and Pitch 1 and Pitch 2, which are 0% to 50%, are selected out of Pitch 1 to Pitch 4 as described above, a value (2, 5) of the associated longitudinal range 1132-4 and a value (−2, 0) of the associated lateral range 1132-5 are obtained.

The time-space determination module 1122 next obtains, from each of the records extracted in Step S1405, the longitudinal value and the lateral value in each set of joint coordinate values (Step S1407), determines whether the obtained values are contained within the longitudinal range and the lateral range, and tallies the number of records having the longitudinal value and the lateral value determined to be contained (Step S1408). The determination in this step may be executed in the manner of Step S904 of FIG. 9.

The time-space determination module 1122 next calculates a proportion of the number of records tallied in Step S1408 to the number of records extracted in Step S1405, and generates a temporal-spatial matching ratio from the proportion (Step S1409).

The time-space determination module 1122 next stores the identification information of the person, the proportion of the pitch (for example, when Pitch 1 and Pitch 2 are selected as described above, "50%" indicating 0% to 50%), and the temporal-spatial matching ratio generated in Step S1409 in the determination result table 1133 (Step S1410).

The time-space determination module 1122 executes the processing steps of Step S1404 to Step S1410 described above for the remaining sets of pitches created by the division in Step S1403. The time-space determination module 1122 further executes the processing described above for every person extracted from the pitch table 1131.

This concludes the processing of the time-space determination module 1122.

Figure 15:
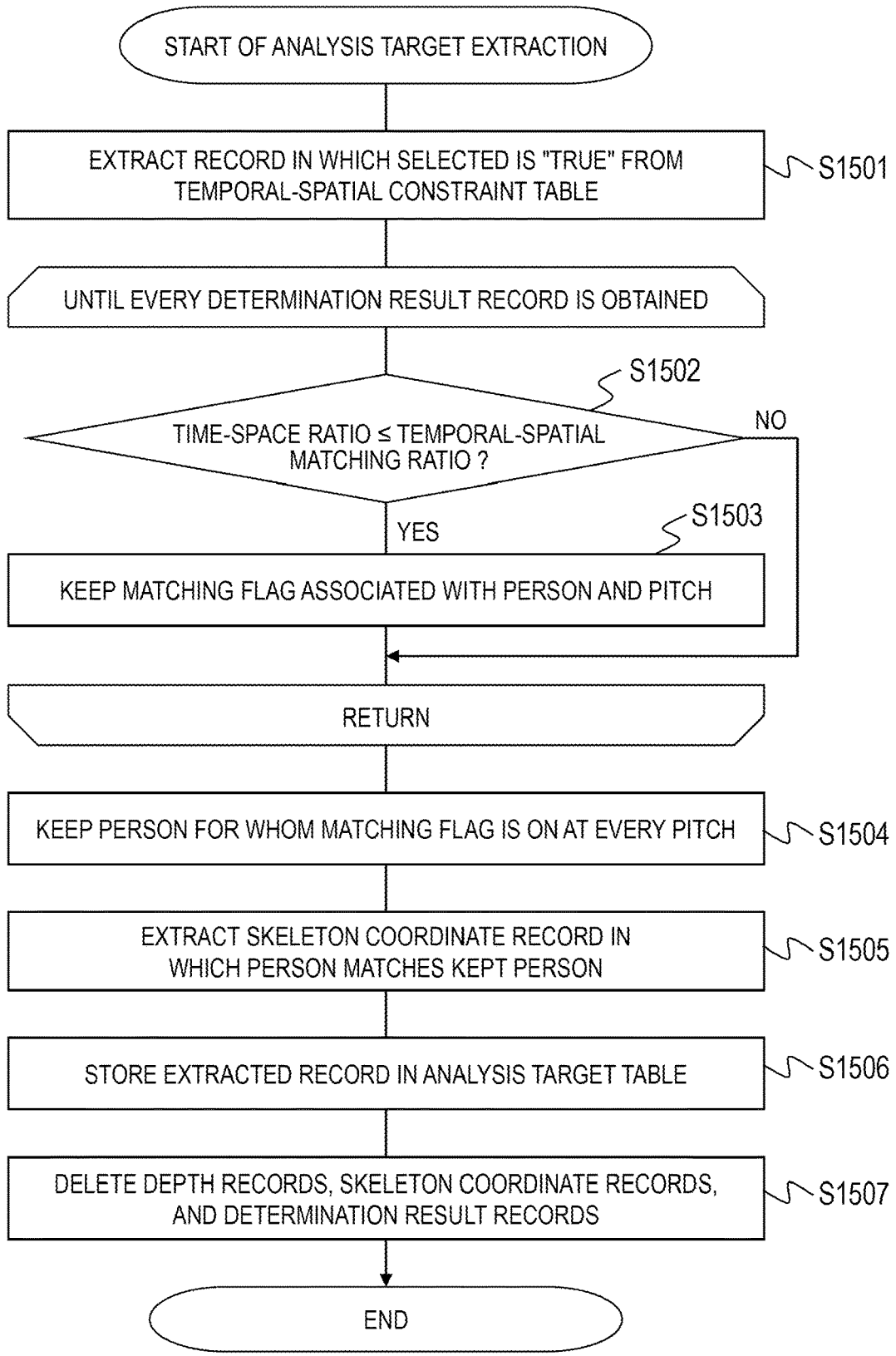
FIG. 15 is a flow chart for illustrating the processing of an analysis target extraction module in the second embodiment.

FIG. 15 is a flow chart for illustrating the processing of the analysis target extraction module 1123 in the second embodiment.

The analysis target extraction module 1123 first refers to the temporal-spatial constraint table 1132 to extract any record in which the selected 1132-2 is "True" (Step S1501).

The analysis target extraction module 1123 next executes the processing steps of Step S1502 and Step S1503 below until every record in the determination result table 1133 is obtained.

First, the analysis target extraction module 1123 obtains a record that has not been obtained from the determination result table 1133, and determines whether the temporal-spatial matching ratio 1133-3 of the obtained record has a value equal to or more than the value of the temporal-spatial matching ratio 1132-6 in a record of the temporal-spatial constraint table 1132 that corresponds to the obtained record (Step S1502). The record of the temporal-spatial constraint table 1132 that corresponds to the obtained record here is a record in which the value of the selected 1132-2 is "True" and the pitch 1132-3 has the same value as the value of the pitch 1133-2 of the obtained record.

When the temporal-spatial matching ratio 1133-3 of the obtained record has a value equal to or more than the value of the temporal-spatial matching ratio 1132-6 in the record of the temporal-spatial constraint table 1132 that corresponds to the obtained record (Step S1502: "Yes"), the analysis target extraction module 1123 keeps a matching flag that is associated with the value of the person 1133 and the value of the pitch 1133-2 of the obtained record (Step S1503).

When the temporal-spatial matching ratio 1133-3 of the obtained record has a value that is not equal to or more than the value of the temporal-spatial matching ratio 1132-6 in the record of the temporal-spatial constraint table 1132 that corresponds to the obtained record (Step S1502: "No"), on the other hand, the analysis target extraction module 1123 does not execute Step S1503.

When the processing steps of Step S1502 and Step S1503 described above are finished for every record in the determination result table 1133, the analysis target extraction module 1123 keeps a person for whom the matching flag is kept at every associated pitch (Step S1504).

How Step S1504 is executed when the temporal-spatial constraint table 1132 shown in FIG. 12 is set and the determination result table 1133 shown in FIG. 12 is obtained is described. With regards to the person "P1," the temporal-spatial matching ratio 1133-3 of the first half is "100%" and is equal to or more than its corresponding threshold value (that is, the value of the temporal-spatial matching ratio 1132-6), which is "90%," but the temporal-spatial matching ratio 1133-3 of the second half is "0%" and is less than its corresponding threshold value, which is "80%." With regards to the person "P2," the temporal-spatial matching ratio 1133-3 of the first half, which is "96%," and the temporal-spatial matching ratio 1133-3 of the second half, which is "90%," are both equal to or more than their corresponding threshold values. With regards to a person "P3," the temporal-spatial matching ratio 1133-3 of the first half, which is "0%," and the temporal-spatial matching ratio 1133-3 of the second half, which is "3%," are both less than their corresponding threshold values. The person "P2" is therefore kept in Step S1504.

Next, the analysis target extraction module 1123 extracts a record in which identification information of the person kept in Step S1504 is recorded as the person 232-2 from the skeleton coordinate table 232 (Step S1505), and stores the extracted record in the analysis target table 251 (Step S1506). The analysis target table 251 is transmitted to the analysis apparatus 100 and is stored in the analysis DB 250.

The analysis target extraction module 1123 then deletes the records finished with the processing described above from the depth table 231, the skeleton coordinate table 232, and the determination result table 1133 (Step S1507). This concludes the processing of the analysis target extraction module 1123.

Figure 16:
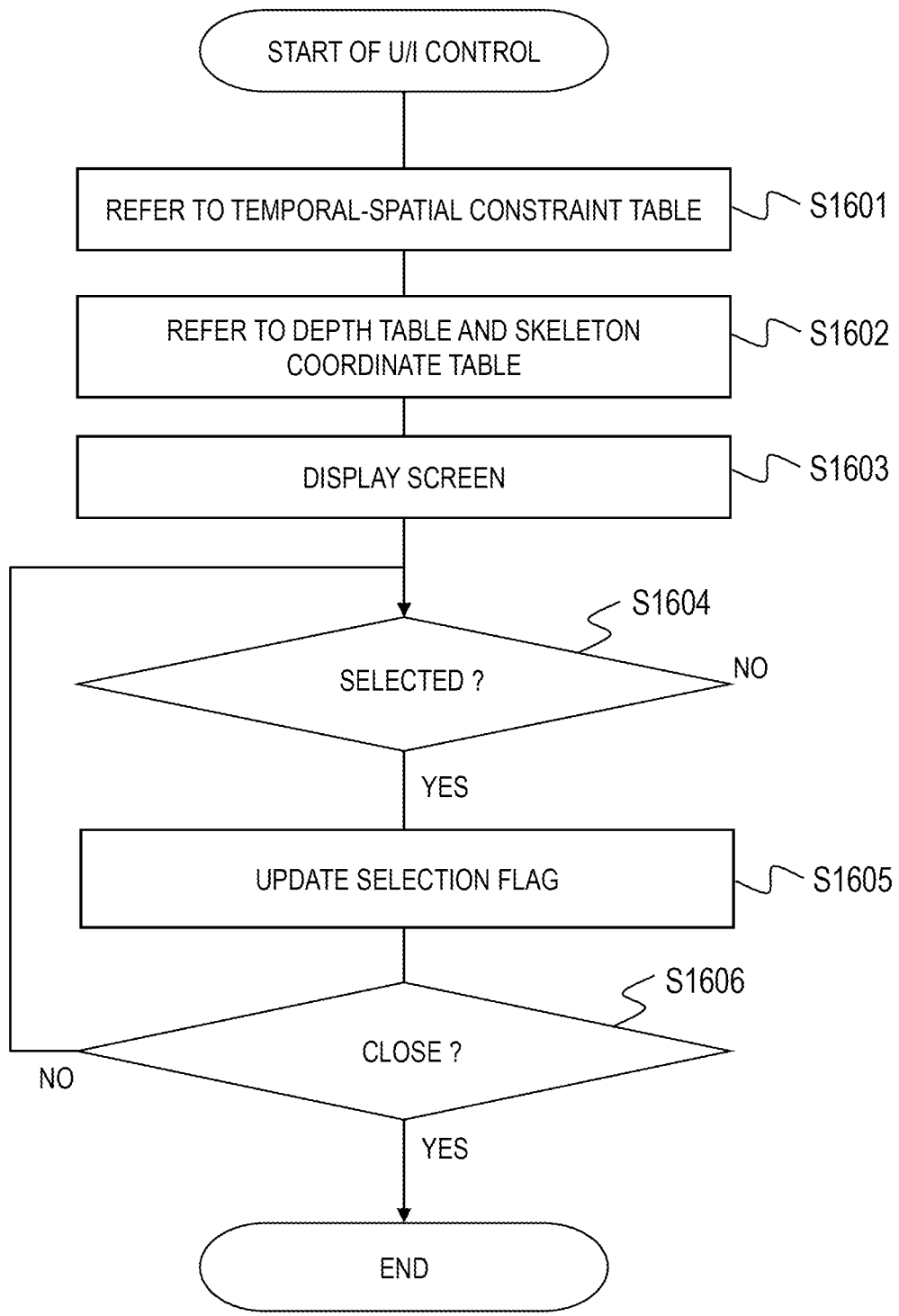
FIG. 16 is a flow chart for illustrating the processing of a U/I control module in the second embodiment.

FIG. 16 is a flow chart for illustrating the processing of the U/I control module 1140 in the second embodiment.

Once the processing is started, the U/I control module 1140 first refers to the temporal-spatial constraint table 1132 (Step S1601), next refers to the depth table 231 and the skeleton coordinate table 232 (Step S1602), and then displays a constraint setting screen (Step S1603). An example of the constraint setting screen is described later with reference to FIG. 17.

The U/I control module 1140 next determines whether some information has been input via the constraint setting screen (Step S1604) and, when there is information that has been input (Step S1604: "Yes"), updates the contents of the table with the input information (Step S1605).

The U/I control module 1140 then determines whether an instruction to close the constraint setting screen has been input (Step S1606) and, when there is no input of the instruction (Step S1606: "No"), the process returns to Step S1604. When it is determined that the instruction to close the constraint setting screen has been input (Step S1606: "Yes"), the U/I control module 1140 ends the processing.

Figure 17:
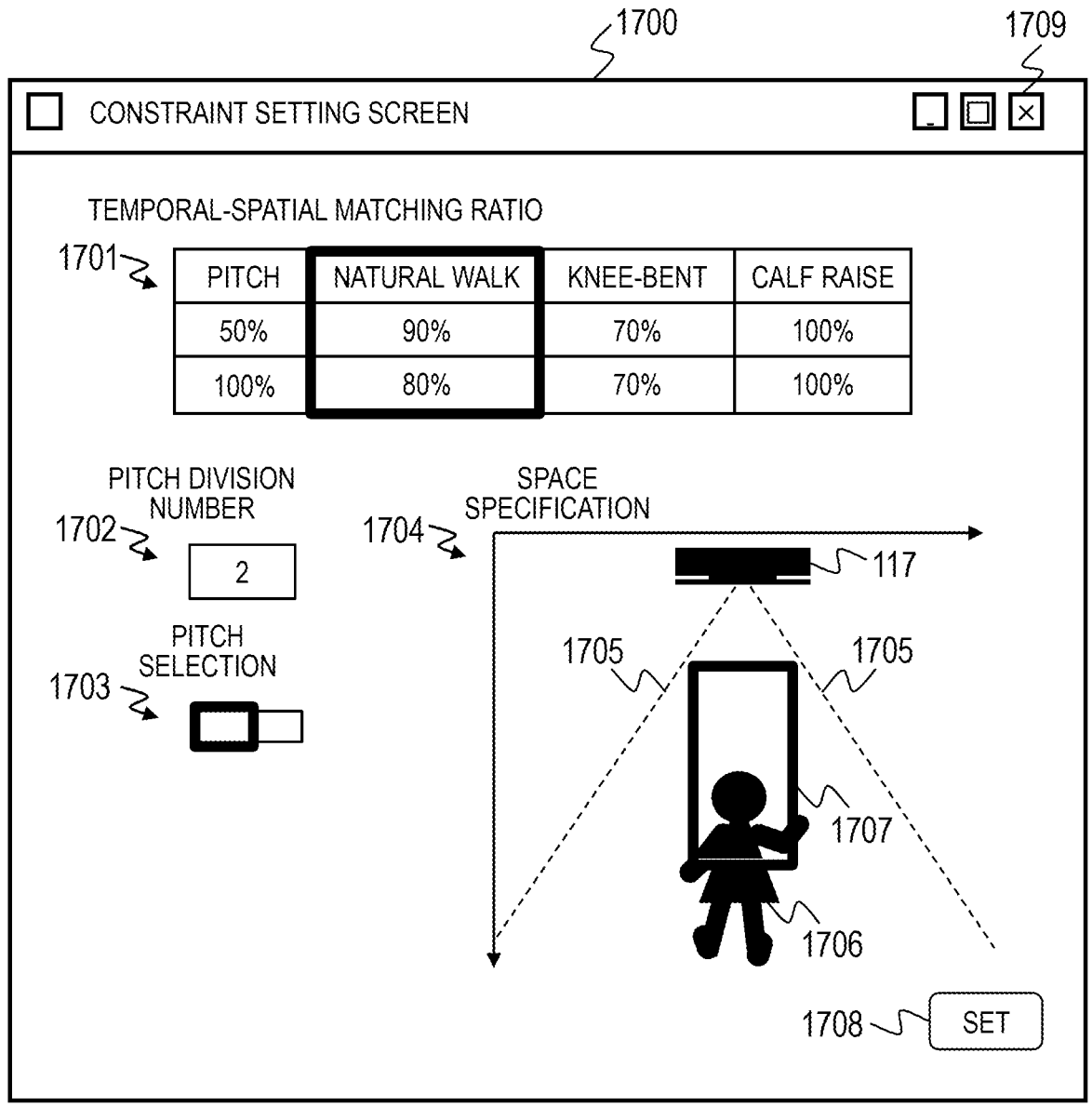
FIG. 17 is an illustration of the constraint setting screen to be displayed in the second embodiment.

FIG. 17 is an illustration of the constraint setting screen to be displayed in the second embodiment.

A constraint setting screen 1700 illustrated in FIG. 17 is a screen displayed by the output apparatus 116, and includes a temporal-spatial matching ratio setting portion 1701, a pitch division number setting portion 1702, a pitch selection portion 1703, a space specification portion 1704, a set button 1708, and a close button 1709.

The temporal-spatial matching ratio setting portion 1701 is an area for setting the temporal-spatial matching ratio 1132-6 for each type of a motion (for example, natural walk, knee-bent walk, and calf raise walk), and for each part created by division of a period in which the motion has been performed based on the proportion of the number of pitches (for example, 0% to 50% or 50% to 100%). A user can input a desired threshold value for the temporal-spatial matching ratio to this area.

The pitch division number setting portion 1702 is an area for setting how many parts a period in which a cyclic motion has been performed is to be divided into. The user can input a desired division count to this area.

The pitch selection portion 1703 is an area for setting pitches of which motion type are to be selected. For example, when the user sets values for one of the motion types in the temporal-spatial matching ratio setting portion 1701 and inputs an instruction to select in the pitch selection portion 1703, the selected 1132-2 associated with the one of the motion types is set to "True."

The space specification portion 1704 is an area for setting the longitudinal range 1132-4 and the lateral range 1132-5 of the temporal-spatial constraint table 1132. For example, a plan view of a space for photographing a motion of an analysis target person 1706 with the photographing apparatus 117 may be displayed in this area. In the example of FIG. 17, the photographing apparatus 117 and a photographing range 1705, which is a range of photographing by the photographing apparatus 117, are displayed. The user operates the input apparatus 115 to set, for example, a position and a size of a rectangle 1707 indicating spatial constraints, and can thus set the longitudinal range 1132-4 and the lateral range 1132-5 in a space marked out by the rectangle 1707.

When the user inputs desired information in the areas described above and operates the set button 1708, the input information is reflected on the temporal-spatial constraint table 1132. When the user operates the close button 1709, the constraint setting screen 1700 is closed.

Although description is omitted in the first embodiment, the contents of the temporal constraint table 241 and the spatial constraint table 242 in the first embodiment can be set with a U/I through a screen in the manner described above.

According to the embodiments of this invention described above, most of motions that do not conform to a measurement protocol assumed by a system can be removed by executing determination with the use of a threshold value on matching ratios of relationships between measurement data and time and between measurement data and space. Required measurement data can thus be extracted without affecting the method of analysis even in an environment prone to noise due to a measurement error and noise due to video capturing an unintended object.

The embodiments of this invention described above include the following examples.

(1) There is provided a measurement apparatus (for example, measurement apparatus 110) including: a processor (for example, processor 111); and a storage unit (for example, at least one of the memory 112 or the storage apparatus 113), the storage unit being configured to hold measurement data (for example, depth table 231) of each time point which is obtained by a photographing apparatus (for example, photographing apparatus 117), and temporal-spatial constraints (for example, temporal constraint table 241 and spatial constraint table 242, or temporal-spatial constraint table 1132). The processor is configured to: extract a position of an object from the measurement data of each time point (for example, processing of skeleton coordinate estimation module 212); determine whether the object satisfies the temporal-spatial constraints (for example, processing of time determination module and space determination module, or processing of time-space determination module); and determine, based on a result of the determination on whether the object satisfies the temporal-spatial constraints, whether the object is an analysis target (for example, processing of analysis target extraction module 223 or analysis target extraction module 1123).

This enables extraction of required data without affecting the method of analysis even in the environment prone to the noise due to the measurement error and the noise due to video capturing an unintended object.

(2) In the above-mentioned item (1), the temporal-spatial constraints may include temporal constraints (for example, temporal constraint table 241) and spatial constraints (for example, spatial constraint table 242). The processor may be configured to: determine whether the object satisfies the temporal constraints (for example, processing of time determination module 221); determine whether the object satisfies the spatial constraints (for example, processing of space determination module 222); and determine, based on a result of the determination on whether the object satisfies the temporal constraints and a result of the determination on whether the object satisfies the spatial constraints, whether the object is an analysis target.

(3) In the above-mentioned item (2), the temporal constraints may include a time range (for example, start time 241-1 and end time 241-2). The processor may be configured to: calculate a temporal matching ratio (for example, temporal matching ratio 243-2) defined as a proportion of pieces of the measurement data having the time point contained within the time range to the measurement data from which the position of the object is extracted; and determine, based on the temporal matching ratio, whether the object satisfies the temporal constraints.

(4) In the above-mentioned item (3), the temporal constraints may include a threshold value for the temporal matching ratio (for example, time ratio 241-3). The processor may be configured to determine that the object satisfies the temporal constraints when the temporal matching ratio is equal to or more than the threshold value for the temporal matching ratio.

(5) In the above-mentioned item (2), the spatial constraints may include a range of a space (for example, longitudinal range 242-1 and lateral range 242-2) contained within a space photographed by the photographing apparatus. The processor may be configured to: calculate a spatial matching ratio (for example, spatial matching ratio 243-3) defined as a proportion of pieces of the measurement data in which the position of the object is contained within the range of the space to the measurement data from which the position of the object is extracted; and determine, based on the spatial matching ratio, whether the object satisfies the spatial constraints.

(6) In the above-mentioned item (5), the spatial constraints may include a threshold value (for example, space ratio 242-3) for the spatial matching ratio. The processor may be configured to determine that the object satisfies the spatial constraints when the spatial matching ratio is equal to or more than the threshold value for the spatial matching ratio.

According to the above-mentioned items (2) to (6), whether an object is an analysis target can be determined by determining whether the object satisfies the temporal constraints and the spatial constraints. With the temporal constraints and the spatial constraints set independently of each other, flexible determination suited to the situation is accomplished.

(7) In the above-mentioned item (1), the temporal-spatial constraints may include a condition (for example, type 1132-1 to pitch 1132-3 of temporal-spatial constraint table 1132) for specifying a time range based on the measurement data, and a space range (for example, longitudinal range 1132-4 and lateral range 1132-5) corresponding to the time range. The processor may be configured to: calculate a temporal-spatial matching ratio (for example, temporal-spatial matching ratio 1133-3) defined as a proportion of pieces of the measurement data in which the position of the object is contained within the space range to the measurement data within the time range specified based on the condition (for example, processing of time-space determination module 1122); and determine, based on the temporal-spatial matching ratio, whether the object satisfies the temporal-spatial constraints.

(8) In the above-mentioned item (7), the temporal-spatial constraints may include a threshold value (for example, temporal-spatial matching ratio 1132-6) for the temporal-spatial matching ratio. The processor may be configured to determine that the object satisfies the temporal-spatial constraints when the temporal-spatial matching ratio is equal to or more than the threshold value for the temporal-spatial matching ratio.

(9) In the above-mentioned item (8), the object may be a person.

Further, the condition for specifying a time range based on the measurement data may include information (for example, type 1132-1 and selected 1132-2) for selecting a type of a motion of a person.

Further, the time range specified based on the condition may be a period (for example, period identified by start time 1131-3 and end time 1131-4 of pitch 1131-2 corresponding to value of pitch 1132-3) specified based on the measurement data as a period in which a person has performed a motion of the selected type.

(10) In the above-mentioned item (9), the condition for specifying a time range based on the measurement data may include information (for example, type 1132-1 and selected 1132-2) for selecting a type of a cyclic motion of a person, and information (for example, pitch 1132-3) specifying a proportion of a number of cycles (for example, pitch) in order to divide a period in which the cyclic motion (for example, walk) has been performed into a plurality of time ranges each of which is the time range specified based on the measurement data, and the space range corresponding to the time range and the threshold value for the temporal-spatial matching ratio may be set for each of the plurality of time ranges (for example, for each of values of pitch 1132-3). The processor may be configured to: specify the plurality of time ranges by dividing the period (for example, of all the pitches of one person stored in pitch table 1131, period from start time 1131-3 of first pitch to end time 1131-4 of last pitch) in which the cyclic motion has been performed, in a manner determined by the specified proportion of the number of cycles, based on the measurement data (into, for example, period of first-half two pitches corresponding to 0% to 50% and period of second-half two pitches corresponding to 50% to 100%); and calculate the temporal-spatial matching ratio for each of the plurality of specified time ranges.

According to the above-mentioned items (7) to (10), a time range appropriate for a motion of an object can be specified, and whether the object is an analysis target can therefore be determined appropriately.

(11) In the above-mentioned item (1), the object may be a person. The processor may be configured to: extract a position of one or more joints of the person (for example, coordinate values of each joint of skeleton coordinate table 232) as the position of the object; and output, as analysis target data (for example, analysis target table 251), the position of one or more joints of a person determined to be the analysis target, the position being extracted from the measurement data.

(12) In the above-mentioned item (11), the photographing apparatus may be a depth camera configured to obtain depth data as the measurement data, and the processor may be configured to extract the position of one or more joints of the person based on the depth data.

(13) In the above-mentioned item (11), the photographing apparatus may be a camera configured to obtain, as the measurement data, video data by one of visible light and invisible light. The processor may be configured to extract the position of one or more joints of the person based on the video data.

According to the above-mentioned items (11) to (13), from a video on which a person who is not an analysis target may accidentally be captured, a person who is an analysis target can be extracted.

This invention is not limited to the embodiments described above, and includes various modification examples. For example, the above-mentioned embodiments have been described in detail for better understanding of this invention, but this invention is not necessarily limited to an invention having all the configurations described above. A part of the configuration of a given embodiment may be replaced with a configuration of another embodiment, or the configuration of another embodiment can be added to the configuration of a given embodiment. It is also possible to add, delete, and replace other configurations for a part of the configuration of each embodiment.

A part or all of each of the above-mentioned configurations, functions, processing modules, processing means, and the like may be implemented by hardware by being designed as, for example, an integrated circuit. Each of the above-mentioned configurations, functions, and the like may be implemented by software by a processor interpreting and executing a program for implementing each function. Information, such as the programs, tables, files, and the like for implementing each of the functions may be stored in a storage device such as a non-volatile semiconductor memory, a hard disk drive, or a solid state drive (SSD), or in a computer-readable non-transitory data storage medium, such as an IC card, an SD card, or a DVD.

The control lines and information lines are illustrated to the extent considered to be required for description, and not all the control lines and information lines on the product are necessarily illustrated. In practice, it may be considered that almost all components are coupled to each other.

What is claimed is:

1. A measurement apparatus, comprising:
a processor; and
one or more memories, the one or more memories being configured to hold measurement data of each time point which is obtained by a photographing apparatus, and temporal-spatial constraints,
wherein the processor is configured to:
extract a position of an object from the measurement data of each time point;
determine whether the object satisfies the temporal-spatial constraints; and
determine, based on a result of the determination on whether the object satisfies the temporal-spatial constraints, whether the object is an analysis target,
wherein the temporal-spatial constraints include a condition for specifying a time range based on the measurement data, and a space range corresponding to the time range,
wherein the processor is configured to:
calculate a temporal-spatial matching ratio defined as a proportion of pieces of the measurement data in which the position of the object is contained within the space range to the measurement data within the time range specified based on the condition; and
determine, based on the temporal-spatial matching ratio, whether the object satisfies the temporal-spatial constraints,
wherein the temporal-spatial constraints include a threshold value for the temporal-spatial matching ratio,
wherein the processor is configured to determine that the object satisfies the temporal-spatial constraints when the temporal-spatial matching ratio is equal to or more than the threshold value for the temporal-spatial matching ratio,
wherein the object is a person,
wherein the condition for specifying the time range based on the measurement data includes information for selecting a type of a motion of the person,
wherein the time range specified based on the condition is a period specified based on the measurement data as a period in which the person has performed a motion of the selected type,
wherein the condition for specifying the time range based on the measurement data includes information for selecting a type of a cyclic motion of the person, and information specifying a proportion of a number of cycles in order to divide a period in which the cyclic motion has been performed into a plurality of time ranges each of which is the time range specified based on the measurement data,
wherein the space range corresponding to the time range and the threshold value for the temporal-spatial matching ratio are set for each of the plurality of time ranges,
wherein the processor is configured to:
specify the plurality of time ranges by dividing the period in which the cyclic motion has been performed, in a manner determined by the specified proportion of the number of cycles, based on the measurement data; and
calculate the temporal-spatial matching ratio for each of the plurality of specified time ranges, and
wherein the processor is further configured to:
extract a position of one or more joints of the person as the position of the object; and
output, as analysis target data, the position of one or more joints of the person determined to be the analysis target, the position being extracted from the measurement data.

2. The measurement apparatus according to claim 1,
wherein the temporal-spatial constraints include temporal constraints that include the time range, and
wherein the processor is configured to:
calculate a temporal matching ratio defined as a proportion of pieces of the measurement data having the time point contained within the time range to the measurement data from which the position of the object is extracted; and
determine, based on the temporal matching ratio, whether the object satisfies the temporal constraints.

3. The measurement apparatus according to claim 2,
wherein the temporal constraints include a threshold value for the temporal matching ratio, and
wherein the processor is configured to determine that the object satisfies the temporal constraints when the temporal matching ratio is equal to or more than the threshold value for the temporal matching ratio.

4. The measurement apparatus according to claim 1,
wherein the temporal-spatial constraints include spatial constraints that include a range of a space contained within a space photographed by the photographing apparatus, and
wherein the processor is configured to:
calculate a spatial matching ratio defined as a proportion of pieces of the measurement data in which the position of the object is contained within the range of the space to the measurement data from which the position of the object is extracted; and
determine, based on the spatial matching ratio, whether the object satisfies the spatial constraints.

5. The measurement apparatus according to claim 4,
wherein the spatial constraints include a threshold value for the spatial matching ratio, and
wherein the processor is configured to determine that the object satisfies the spatial constraints when the spatial matching ratio is equal to or more than the threshold value for the spatial matching ratio.

6. The measurement apparatus according to claim 1,
wherein the photographing apparatus is a depth camera configured to obtain depth data as the measurement data, and
wherein the processor is configured to extract the position of one or more joints of the person based on the depth data.

7. A measurement apparatus comprising:
a processor; and
one or more memories, the one or more memories being configured to hold measurement data of each time point which is obtained by a photographing apparatus, and temporal-spatial constraints,
wherein the processor is configured to:
extract a position of an object from the measurement data of each time point;

determine whether the object satisfies the temporal-spatial constraints; and determine, based on a result of the determination on whether the object satisfies the temporal-spatial constraints, whether the object is an analysis target, wherein the temporal-spatial constraints include a condition for specifying a time range based on the measurement data, and a space range corresponding to the time range, wherein the processor is configured to:
  calculate a temporal-spatial matching ratio defined as a proportion of pieces of the measurement data in which the position of the object is contained within the space range to the measurement data within the time range specified based on the condition; and
  determine, based on the temporal-spatial matching ratio, whether the object satisfies the temporal-spatial constraints, wherein the temporal-spatial constraints include a threshold value for the temporal-spatial matching ratio, wherein the processor is configured to determine that the object satisfies the temporal-spatial constraints when the temporal-spatial matching ratio is equal to or more than the threshold value for the temporal-spatial matching ratio, wherein the object is a person, wherein the condition for specifying the time range based on the measurement data includes information for selecting a type of a motion of the person, wherein the time range specified based on the condition is a period specified based on the measurement data as a period in which the person has performed a motion of the selected type, wherein the condition for specifying the time range based on the measurement data includes information for selecting a type of a cyclic motion of the person, and information specifying a proportion of a number of cycles in order to divide a period in which the cyclic motion has been performed into a plurality of time ranges each of which is the time range specified based on the measurement data, wherein the space range corresponding to the time range and the threshold value for the temporal-spatial matching ratio are set for each of the plurality of time ranges, and wherein the processor is configured to:
  specify the plurality of time ranges by dividing the period in which the cyclic motion has been performed, in a manner determined by the specified proportion of the number of cycles, based on the measurement data; and
  calculate the temporal-spatial matching ratio for each of the plurality of specified time ranges.

8. A measurement method to be executed by a measurement apparatus comprising a processor and one or more memories, the one or more memories being configured to hold measurement data of each time point which is obtained by a photographing apparatus, and temporal-spatial constraints, the measurement method comprising:
  extracting, by the processor, a position of an object from the measurement data of each time point;
  determining, by the processor, whether the object satisfies the temporal-spatial constraints; and
  determining, by the processor, based on a result of the determination on whether the object satisfies the temporal-spatial constraints, whether the object is an analysis target, wherein the temporal-spatial constraints include a condition for specifying a time range based on the measurement data, and a space range corresponding to the time range, wherein the measurement method comprises:
  calculating, by the processor, a temporal-spatial matching ratio defined as a proportion of pieces of the measurement data in which the position of the object is contained within the space range to the measurement data within the time range specified based on the condition; and
  determining, by the processor, based on the temporal-spatial matching ratio, whether the object satisfies the temporal-spatial constraints, wherein the temporal-spatial constraints include a threshold value for the temporal-spatial matching ratio, wherein the measurement method comprises determining, by the processor, that the object satisfies the temporal-spatial constraints when the temporal-spatial matching ratio is equal to or more than the threshold value for the temporal-spatial matching ratio, wherein the object is a person, wherein the condition for specifying the time range based on the measurement data includes information for selecting a type of a motion of the person, wherein the time range specified based on the condition is a period specified based on the measurement data as a period in which the person has performed a motion of the selected type, wherein the condition for specifying the time range based on the measurement data includes information for selecting a type of a cyclic motion of the person, and information specifying a proportion of a number of cycles in order to divide a period in which the cyclic motion has been performed into a plurality of time ranges each of which is the time range specified based on the measurement data, wherein the space range corresponding to the time range and the threshold value for the temporal-spatial matching ratio are set for each of the plurality of time ranges, wherein the measurement method comprises:
  specifying, by the processor, the plurality of time ranges by dividing the period in which the cyclic motion has been performed, in a manner determined by the specified proportion of the number of cycles, based on the measurement data; and
  calculating, by the processor, the temporal-spatial matching ratio for each of the plurality of specified time ranges, and wherein the measurement method further comprises:
  extracting, by the processor, a position of one or more joints of the person as the position of the object; and
  outputting, as analysis target data, the position of one or more joints of the person determined to be the analysis target, the position being extracted from the measurement data.

* * * * *